(12) United States Patent
Bouhadir et al.

(10) Patent No.: US 11,833,224 B1
(45) Date of Patent: Dec. 5, 2023

(54) LYOPROTECTANT COMPOSITIONS AND USES THEREOF

(71) Applicant: Leuvian LLC, Pinecrest, FL (US)

(72) Inventors: Spencer Bouhadir, Lake Worth, FL (US); Jacob J. Miguel, Miami, FL (US)

(73) Assignee: LEUVIAN LLC, Pinecrest, FL (US)

( * ) Notice: Subject to any disclaimer, the term of this patent is extended or adjusted under 35 U.S.C. 154(b) by 0 days.

(21) Appl. No.: 18/166,416

(22) Filed: Feb. 8, 2023

(51) Int. Cl.
*A61K 47/69* (2017.01)
*A61K 9/19* (2006.01)
*A61K 47/18* (2017.01)
*B82Y 5/00* (2011.01)
*A61K 47/26* (2006.01)

(52) U.S. Cl.
CPC ............ *A61K 47/6951* (2017.08); *A61K 9/19* (2013.01); *A61K 47/183* (2013.01); *A61K 47/26* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 5,445,813 A | 8/1995 | Schneider et al. | |
| 6,284,282 B1* | 9/2001 | Maa | A61K 38/30 514/8.4 |
| 9,872,848 B2 | 1/2018 | Troiano et al. | |
| 9,877,923 B2 | 1/2018 | Figueiredo et al. | |
| 10,537,622 B2 | 1/2020 | Bioley et al. | |
| 10,835,494 B2 | 11/2020 | López Machado et al. | |
| 2011/0237686 A1* | 9/2011 | Ng | A61K 9/5146 264/28 |
| 2012/0121580 A1* | 5/2012 | Bhambhani | A61K 9/08 424/130.1 |
| 2014/0099263 A1 | 4/2014 | Eliasof et al. | |
| 2015/0308988 A1 | 10/2015 | Babuka et al. | |
| 2016/0130606 A1 | 5/2016 | Buschmann et al. | |
| 2017/0182081 A1 | 6/2017 | Mutzke | |
| 2021/0177857 A1 | 6/2021 | Bagrodia et al. | |
| 2022/0001021 A1 | 1/2022 | Uhl et al. | |
| 2022/0202718 A1 | 6/2022 | Guild et al. | |
| 2022/0273796 A1* | 9/2022 | Dubey | C07K 16/2878 |

FOREIGN PATENT DOCUMENTS

| | | |
|---|---|---|
| WO | WO-97/21448 A1 | 6/1997 |
| WO | WO-2005/123034 A2 | 12/2005 |
| WO | WO-2011/069528 A1 | 6/2011 |

OTHER PUBLICATIONS

Shaffei et al. (A comprehensive Review on the Applications of Exosomes and Liposomes in Regenerative Medicine and Tissue Engineering, Polymers, Jul. 30, 2021). (Year: 2021).*

Susa, Francesca, et al. "Enhancing the Preservation of Liposomes: The Role of Cryoprotectants, Lipid Formulations and Freezing Approaches," Cryobiology, vol. 98, 2021, pp. 46-56., https://doi.org/10.1016/j.cryobiol.2020.12.009.

* cited by examiner

*Primary Examiner* — Melissa S Mercier
(74) *Attorney, Agent, or Firm* — FOLEY & LARDNER LLP

(57) ABSTRACT

Provided herein are compositions that are useful in stabilizing and preserving biologic drugs, such as exosomes, during lyophilization. Further provided herein are methods for stabilizing biologic drugs during lyophilization using the compositions of the disclosure.

17 Claims, 12 Drawing Sheets

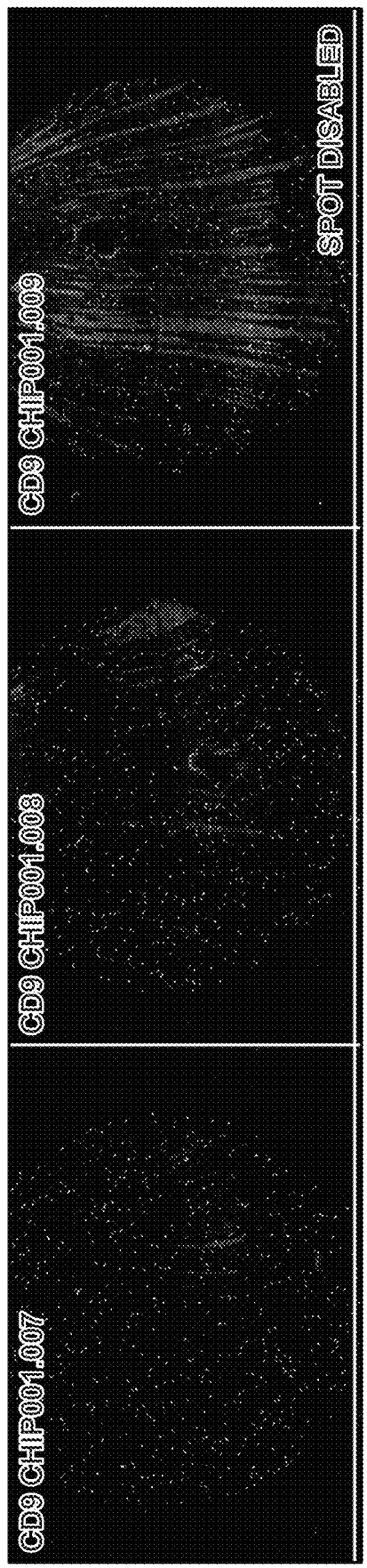
FIG. 6A  Sample B
FIG. 6B  Sample C
FIG. 6C  Sample F

LYOPROTECTANT COMPOSITIONS AND USES THEREOF

BACKGROUND

The present disclosure relates generally to the field of compositions that protect biologic drugs, e.g., exosomes, liposomes or niosomes, during the lyophilization process. The lyophilization process is especially harsh for biologic drugs that comprise membranes. The conventional lyoprotectants result in loss of integrity (e.g., loss of membrane integrity) during lyophilization. There is a need for improved lyoprotectant compositions and improved methods for lyoprotection, especially for biologic drugs comprising membranes.

Extracellular vesicles (EV) are small structures enclosed in lipid bilayers (40-250 nm) that are actively secreted by various types of cells into the extracellular environment. An extensive range of biofluids contains EV, including plasma, whole blood, urine, saliva, lymph, cerebrospinal fluid, seminal, abdominal, thoracic fluid, breast milk, as well as interstitial tissues. In addition to their role in intercellular communication, they are also involved in a wide variety of physiological and pathological processes. Because of their relative complexity, composition, and role in body homeostasis, EVs have been used in biomarkers, regenerative medicine, drug delivery, immunotherapy, and vaccine development studies.

Although extracellular vesicles (e.g., exosomes) are generally stored at −80° C., this temperature is not suitable for their handling or transportation and, therefore, other storage methods are desirable. Lyophilization is a promising storage method that can be used to preserve various substances at room temperature. However, current lyoprotectant compositions do not provide adequate protection during the freeze drying process in terms of stability and membrane integrity. Improved lyoprotectant compositions that prevent aggregation, improve bioavailability, increase stability and improve membrane integrity (i.e., improve cargo retention) are needed.

SUMMARY OF THE DISCLOSURE

An aspect of the disclosure relates to a composition comprising: 0.3%-8% cyclic oligosaccharide-based polymer, 2%-10% sugar, and 0.2%-10% amino acid. In some embodiments, the composition is useful for preserving the integrity of extracellular vesicles (EVs) (such as exosomes) or lipid-based delivery vehicles (such as liposomes or niosomes) during lyophilization. In some embodiments, an EV or a lipid-based delivery vehicle that is lyophilized in the compositions of the instant disclosure retain the shape, structural integrity and function after lyophilization and resuspension (i.e., pre and post lyophilization shape, structural integrity and function are essentially the same).

In some embodiments, the cyclic oligosaccharide-based polymer comprises an alpha cyclodextrin, beta cyclodextrin, a gamma cyclodextrin, a 2-hydroxypropyl-β-cyclodextrin, a β-cyclodextrin sulfobutylether, or any derivative thereof, and any combination thereof. In a specific embodiment, the cyclic oligosaccharide-based polymer comprises gamma cyclodextrin.

In some embodiments, the sugar comprises sucrose, mannitol, or trehalose. In a specific embodiment, the sugar comprises sucrose.

In some embodiments, the amino acid comprises trimethylglycine, glycine, arginine or any salts thereof. In a specific embodiment, the amino acid comprises trimethylglycine.

In some embodiments, the composition further comprises a biologic drug. In some embodiments, the biologic drug comprises an exosome, a liposome or a niosome. In a specific embodiment, the biologic drug comprises an exosome.

In some embodiments, the cyclic oligosaccharide-based polymer comprises gamma cyclodextrin, wherein the sugar comprises sucrose, wherein the amino acid comprises trimethylglycine, and wherein the biologic drug comprises an exosome.

In some embodiments, the composition comprises about 6% sucrose, about 1% gamma cyclodextrin and about 1% trimethylglycine and an exosome.

In some embodiments, the composition is lyophilized.

Another aspect of the disclosure is directed to a method for stabilizing a biologic drug during lyophilization comprising mixing the biologic drug with a lyoprotectant blend before lyophilization, wherein the lyoprotectant blend comprises: 0.3%-8% cyclic oligosaccharide-based polymer, 2%-10% sugar, and 0.2%-10% amino acid.

In some embodiments, the cyclic oligosaccharide-based polymer comprises an alpha cyclodextrin, beta cyclodextrin, a gamma cyclodextrin, a 2-hydroxypropyl-β-cyclodextrin, a β-cyclodextrin sulfobutylether, or any derivative thereof, and any combination thereof. In a specific embodiment, the cyclic oligosaccharide-based polymer comprises gamma cyclodextrin.

In some embodiments, the sugar comprises sucrose, mannitol, or trehalose. In a specific embodiment, the sugar comprises sucrose.

In some embodiments, the amino acid comprises trimethylglycine, glycine, arginine or any salts thereof. In a specific embodiment, the amino acid comprises trimethylglycine.

In some embodiments, the biologic drug comprises an exosome, a liposome or a niosome. In a specific embodiment, the biologic drug comprises an exosome.

In some embodiments, the cyclic oligosaccharide-based polymer comprises gamma cyclodextrin, wherein the sugar comprises sucrose, wherein the amino acid comprises trimethylglycine, wherein the biologic drug comprises an exosome.

In some embodiments, the lyoprotectant blend comprises about 6% sucrose, about 1% gamma cyclodextrin and about 1% trimethylglycine and an exosome.

In some embodiments, the mixture of the biologic drug and the lyoprotectant blend are lyophilized.

In some embodiments, the exosome stabilized by the method during lyophilization retains at least 90% of its structural integrity when resolubilized.

Figure 1A:
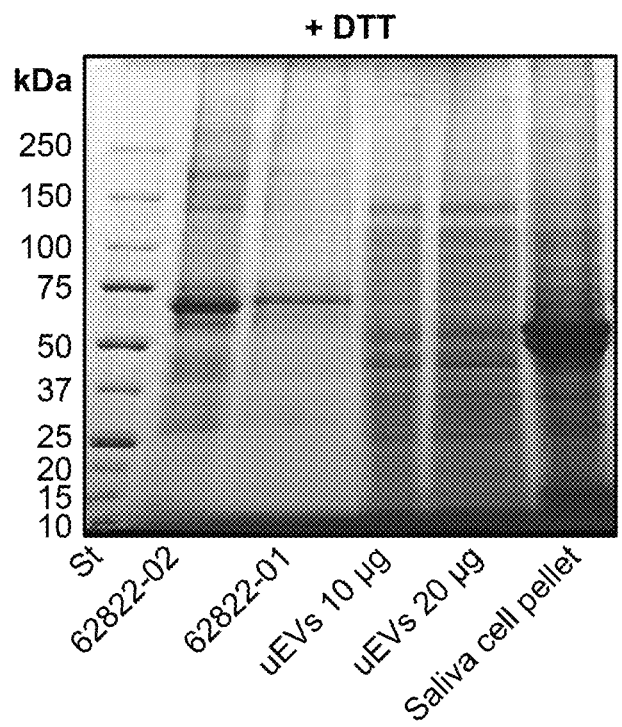
FIGS. 1A-1C show Coomassie staining of test exosome samples. Ten μg (or twenty μg where indicated) of protein was loaded per lane. (A) 62822-02: Liquid control exosome sample, 62822-01: Liquid (non-lyophilized) exosome sample in lyoprotectant comprising 5% Mannitol (5% Mannitol represents the conventional lyoprotectant composition), uEVs: 10 or 20 μg Urinary extracellular vesicles (uEVs), as well as a saliva cell pellet sample. (B) The following samples were run on an acrylamide gel in the presence of DTT and Coomassie stained: Sample A: Lyophilized exosome sample in 6% sucrose, 2% gamma cyclodextrin; Sample B: Lyophilized exosome sample in 5% mannitol; Sample C: liquid control exosome sample; Sample E: Lyophilized exosome sample in 4% sucrose and 1% gamma cyclodextrin; Sample F: Lyophilized exosome sample in 6% sucrose, 1% gamma cyclodextrin and 1% trimethylglycine (TMG); Sample A_P100: Sample A after ultracentrifugation (UC); Sample B_P100: Sample B after ultracentrifugation (UC); Sample C_P100: Sample C after ultracentrifugation (UC). (C) The following samples were run on an acrylamide gel in the absence of DTT (except Sample B) and Coomassie stained: Sample A: Lyophilized exosome sample in 6% sucrose, 2% gamma cyclodextrin; Sample B: Lyophilized exosome sample in 5% mannitol; Sample C: liquid control exosome sample; Sample E: Lyophilized exosome sample in 4% sucrose and 1% gamma cyclodextrin; Sample F: Lyophilized exosome sample in 6% sucrose, 1% gamma cyclodextrin and 1% trimethylglycine (TMG). Sample B (*) with DTT was loaded in the lane. UC: ultracentrifugation pellets. uEV urinary extracellular vesicle were used as positive control and Saliva low centrifugation pellet was used as cellular positive control for the detection of calnexin as endoplasmic reticulum marker. St: molecular weight standard.
Figure 1B:
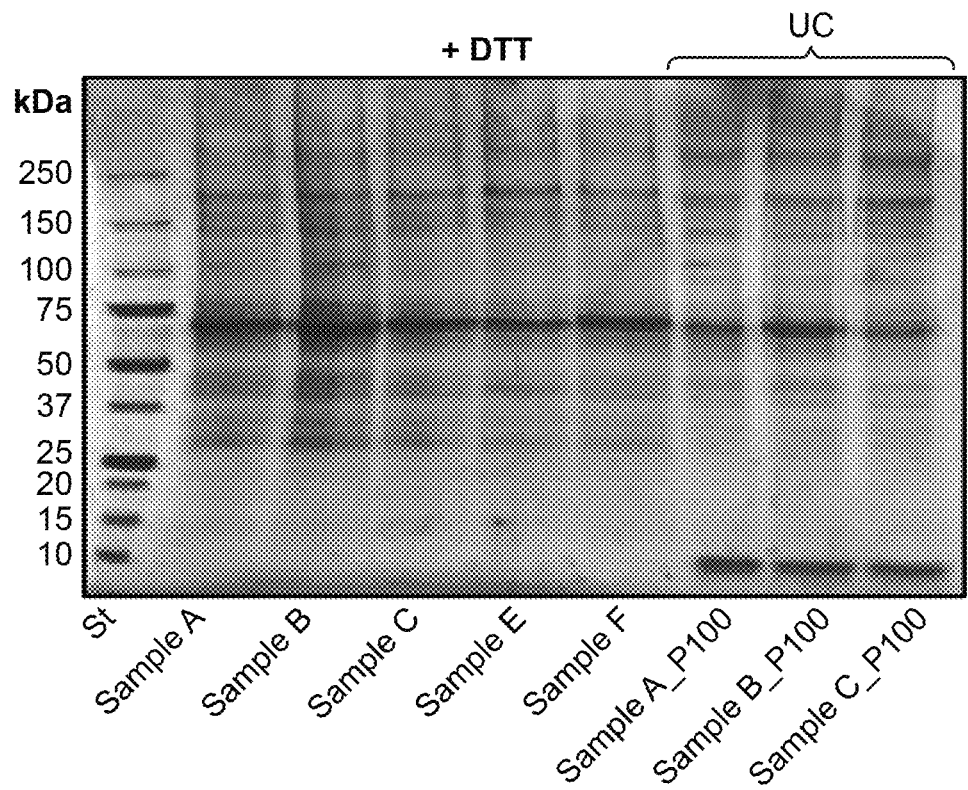
Figure 1C:
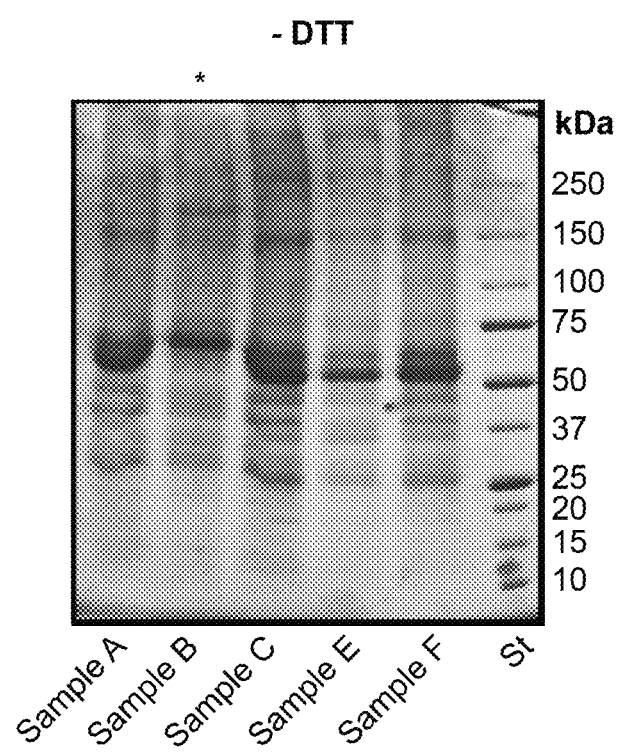
Figure 2:
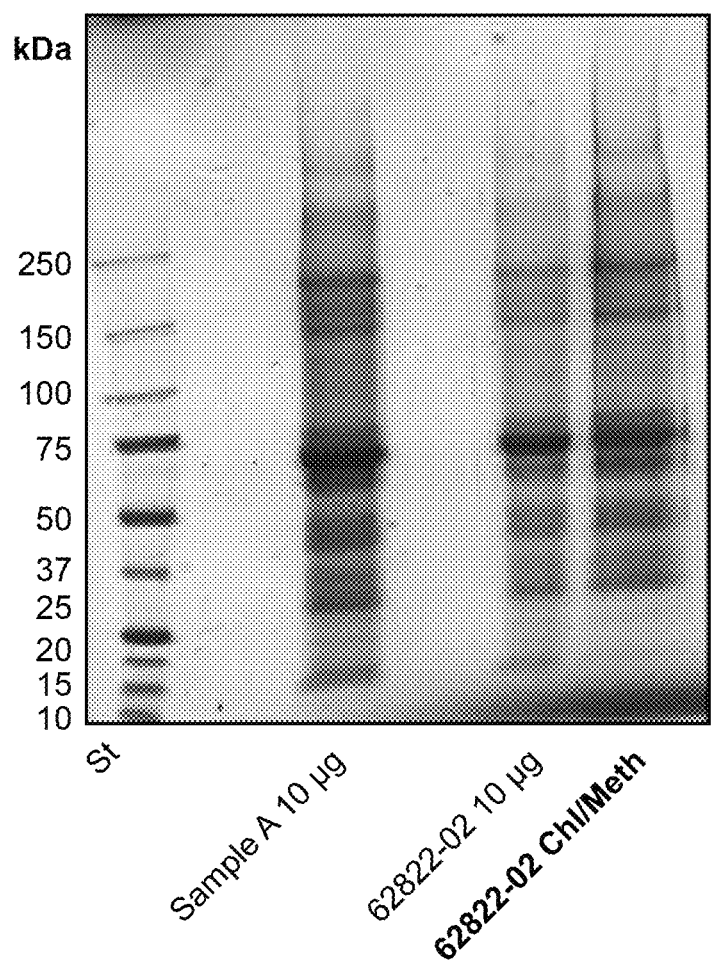
Figure 3A:
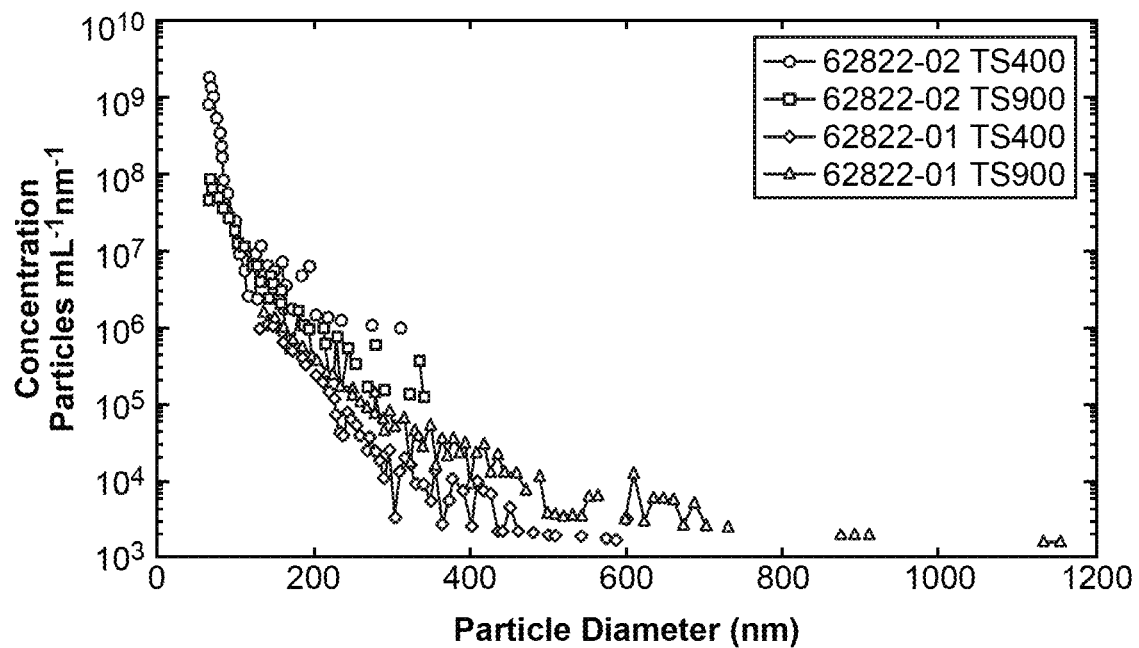
Figure 3B:
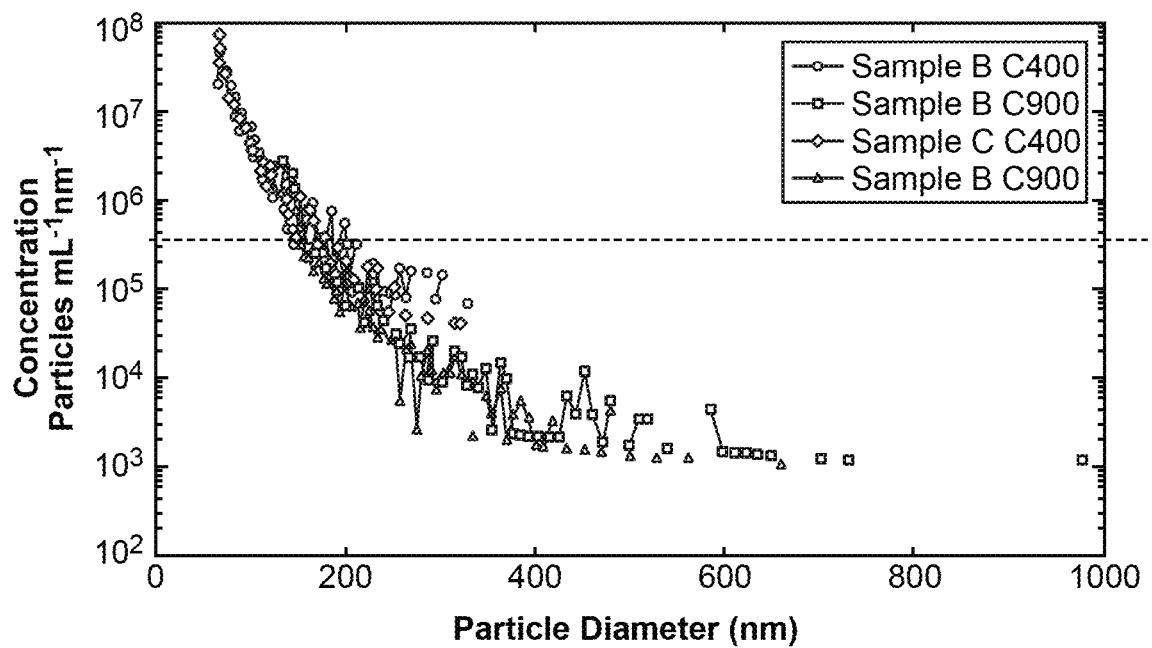
Figure 3C:
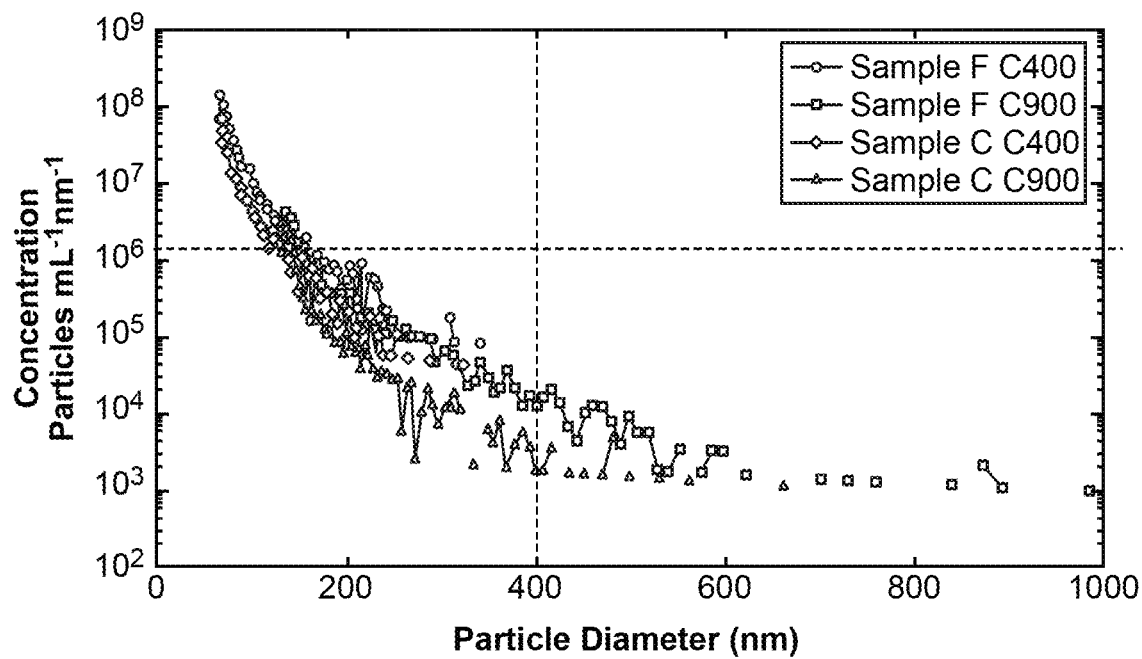
Figure 3D:
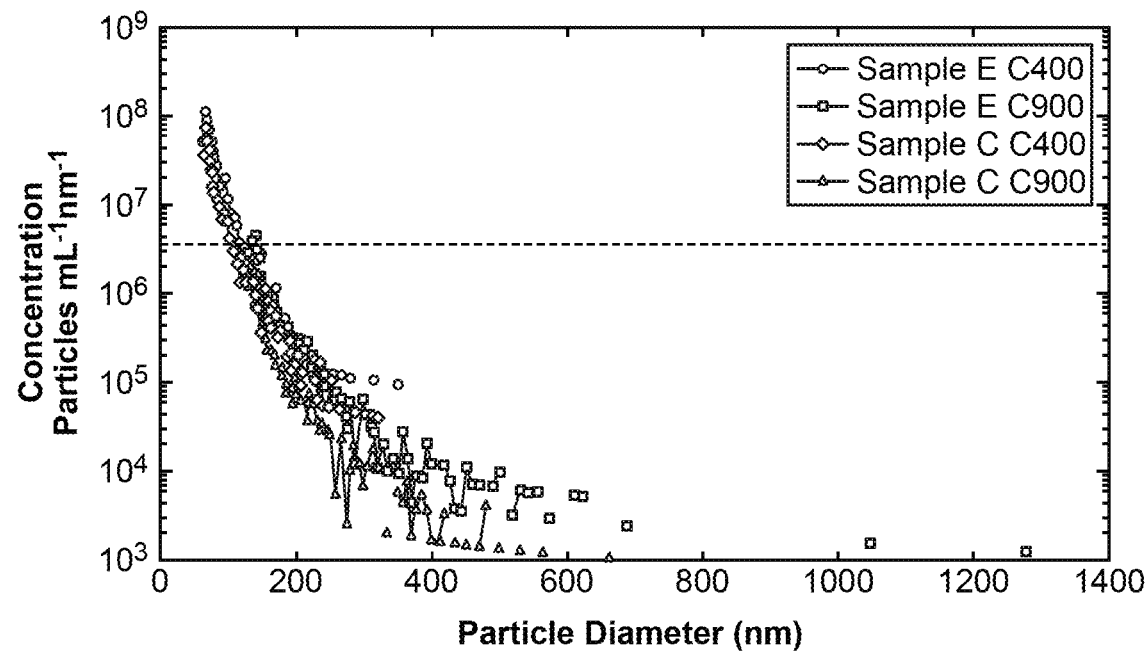

FIG. 2 shows Coomassie staining of the samples submitted to MS: Sample A, and 62822-02 as described in FIGS. 1, and 62822-02 sample treated with chroloform and methanol (622822-02 Chl/Meth).

FIGS. 3A-3D show Concentration Spectral Density (CSD) analyses of (A) 62822-02 TS400, 62822-02 TS900, 62822-01 TS400, 62822-01 TS900; (B) Sample B C400, Sample B C900, Sample C C400, Sample C C900; (C) Sample F C400, Sample F C900, Sample C C400, Sample C C900; and (D) Sample E C400, Sample E C900, Sample C C400, Sample C C900.

FIGS. 4A-4F show Particle phenotyping of the samples. (SP-IRIS) fluorescence detection using as capture antibodies mouse anti human-CD9, anti-CD81, anti-CD63 and mouse isotype control. Same clones of antibodies: anti-CD81-AF555, anti-CD9-AF488 and anti-CD63-AF647 were used for a multiparametric detection. Each figure (A)-(F) has four capture clusters CD9, CD81, CD63 and isotype control (MIgG). Within each cluster, the first (leftmost) column shows the total number of captured particles; the second column shows the number of CD63+particles, the third column shows the number of CD81+particles, the fourth column shows the number of CD9+particles; and the fifth (rightmost) column shows non-specific binding by mouse IgG. (A) Sample 628822-02; (B) Sample 622800-01; (C) Sample A, (D) Sample C; (E) Sample E; and (F) Sample F.

FIGS. 5A-5F show data analysis of FIGS. 4A-4F. The data from FIG. 5 were analyzed in depth to determine the tetraspanins distribution of single, double and triple-positive (CD81, CD9, CD63) EVs captured onto the CD81, CD63, and CD9 antibodies. (A) Sample 628822-02; (B) Sample 622800-01; (C) Sample A, (D) Sample C; (E) Sample E; and (F) Sample F.

FIGS. 6A-6C show representative CD9 captured exosomes from exosome samples (A) Sample B, (B) Sample C, and (C) Sample F stained with CD9 Ab. While Sample B shows very few CD9+ exosomes, Sample F showed an enrichment of CD9+exosomes, showing that Sample F protected the integrity of the exosomes during lyophilization.

Figure 7:
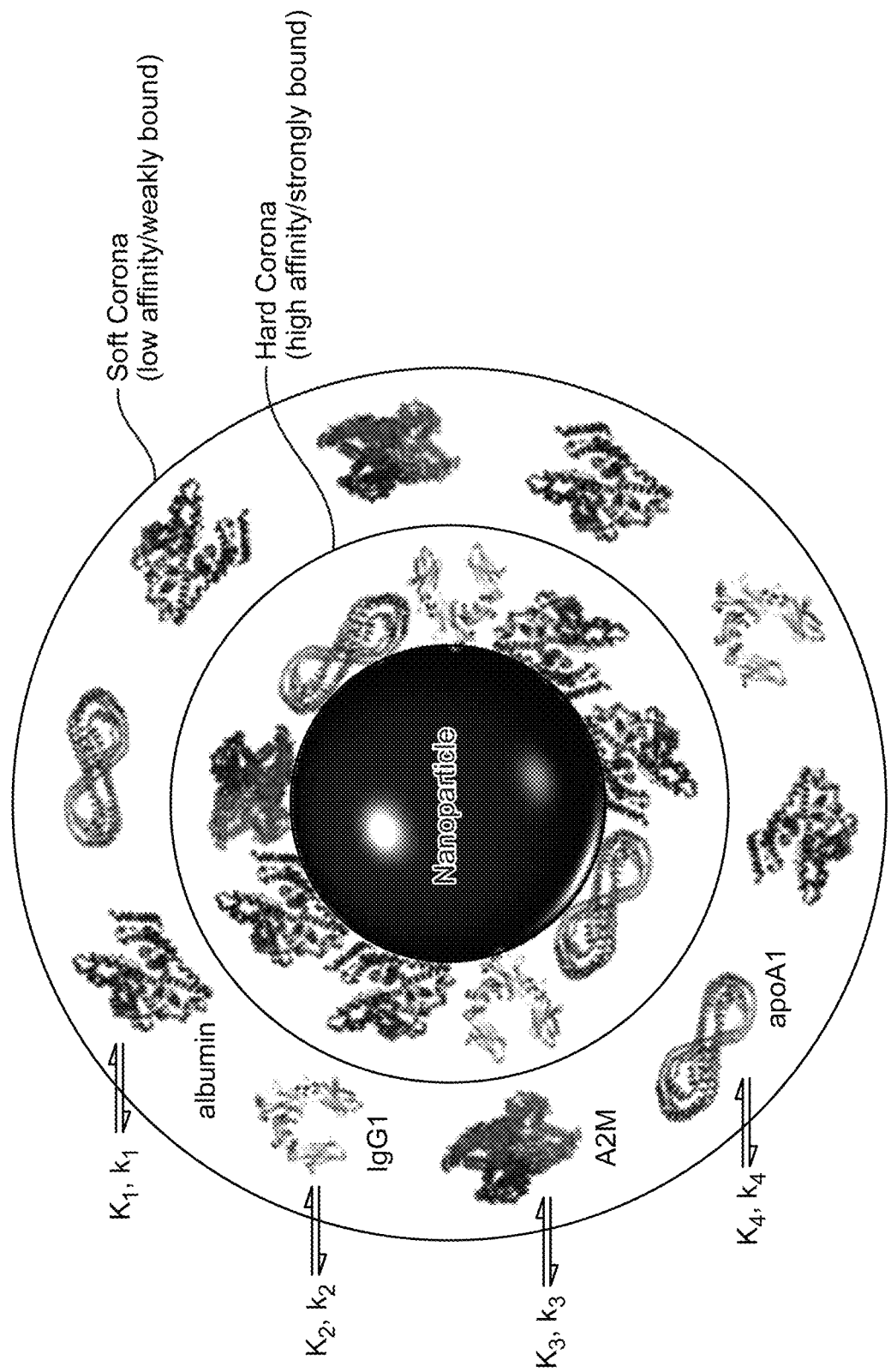

FIG. 7 shows a schematic of protein corona formation on a nanoparticle surface. Protein adsorption is a kinetic and themodynamic function of both the individual proteins and nanoparticle properties such as surface modification, composition and diameter. Hard coronas have higher-affinity proteins that are irreversibly bonded to the nanoparticle surface, while soft coronas have lower-affinity proteins on the nanoparticle surface that are reversibly bound. Serum proteins commonly observed in nanoparticle coronas are shown as a representative corona: serum albumin, immunoglobulinG1 (IgG1), alpha-2 macroglobulin (A2M), and apolipoprotein A-1 (apolA1).

DETAILED DESCRIPTION

Definitions

The term "about" is used here in conjunction with numeric values to include normal variations in measurements as expected by persons skilled in the art, and is understood have the same meaning as "approximately" and to cover a typical margin of error, such as ±5% of the stated value.

Terms such as "a," "an," and "the" are not intended to refer to only a singular entity, but include the general class of which a specific example may be used for illustration.

The terms "a," "an," and "the" are used interchangeably with the term "at least one." The phrases "at least one of" and "comprises at least one of" followed by a list refers to any one of the items in the list and any combination of two or more items in the list.

As used here, the term "or" is generally employed in its usual sense including "and/or" unless the content clearly dictates otherwise. The term "and/or" means one or all of the listed elements or a combination y two or more of the listed elements.

Any amounts (e.g., concentrations) of components in a composition given as a percentage (%) refer to a percentage by weight per volume unless otherwise indicated.

As used herein the term "exosome" refers to a cell-derived small (between 20-300 nm in diameter, more preferably 40-200 nm in diameter) vesicle comprising a membrane that encloses an internal space, and which is generated from said cell by direct plasma membrane budding or by fusion of the late endosome with the plasma membrane. The exosome is a species of extracellular vesicle. The exosome comprises lipid or fatty acid and polypeptide and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. The exosome can be derived from a producer cell, and isolated from the producer cell based on its size, density, biochemical parameters, or a combination thereof.

As used herein, the term "lyophilization" (also known as "lyophilizing," "freeze drying" or "cryodessication") refers to a low temperature dehydration process that involves freezing a product and lowering pressure, removing the ice by sublimation. Lyophilizing may comprise freezing the composition at a temperature of greater than ~40° C., or e.g. less than ~30° C., forming a frozen composition; and drying the frozen composition to form the lyophilized composition. The step of drying may occur at 50 mTorr at a temperature of –25 to –34° C., or –30 to –34° C.

As used herein, the term, "lyoprotection", refers to stabilization during all of the freeze-drying process (i.e., during both freezing and drying). Such stabilization is often required for freeze-drying of biological materials such as proteins, peptides and biological drugs. This is because complex biological molecules often require a moderate level of residual water to maintain structure and function. Accordingly, a "lyoprotectant" protects the structure and/or function of biologic drugs during lyophilization (e.g., prevents aggregation, improves bioavailability, increases stability and/or improves membrane integrity and cargo retention).

As used herein, the term "liposome" refers to a generally spherical cluster or aggregate of amphiphilic compounds (including lipid compounds), generally in the form of one or more concentric layers (e.g., bilayers).

As used herein the term "niosome" refers to a unilamellar or multilamellar vesicle comprising non-ionic surfactants, and optionally cholesterol and a charged molecule. In some embodiments, the no-ionic surfactants comprise alkyl ethers, alkyl esters, alkyl amides, fatty acid and amino acid compounds. In some embodiments, niosomes of the instant disclosure comprises no phospholipid as a component of the membrane.

Compositions

The instant disclosure provides compositions that can protect biologic drug integrity and/or structure during lyophilization. Biologic drugs lyophilized using the compositions of the instant disclosure retain at least 90%, 91%, 92%, 93%, 94%, 95%, 96%, 97%, 98%, 99% or more of their biological activity and/or integrity when reconstituted/thawed. In a specific embodiment, the compositions of the instant disclosure are effective at protecting biological activity and/or structural integrity of exosomes at least 90%, 91%, 92%, 93%, 94%, 95%, 96%, 97%, 98%, 99% or more as compared to exosomes that have not been lyophilized.

An aspect of the disclosure is directed to a lyoprotectant composition comprising 0.3%-8% (e.g., 0.3, 0.5, 0.7, 0.9, 1, 1.2, 1.5, 1.7, 2, 2.2, 2.5, 2.7, 3, 3.2, 3.5, 3.7, 4, 4.2, 4.5, 4.7, 5, 5.2, 5.5, 5.7, 6, 6.2, 6.5, 6.7, 7, 7.2, 7.5, 7.7, 8%, or any value therebetween) cyclic oligosaccharide-based polymer, 2%-10% (e.g., 2, 2.2, 2.5, 2.7, 3, 3.2, 3.5, 3.7, 4, 4.2, 4.5, 4.7, 5, 5.2, 5.5, 5.7, 6, 6.2, 6.5, 6.7, 7, 7.2, 7.5, 7.7, or 8, 8.2, 8.5, 8.7, 9, 9.2, 9.5, 9.7, 9.9, 10%, or any value therebetween) sugar, and 0.2%-10% (e.g., 0.2, 0.3, 0.5, 0.7, 0.9, 1, 1.2, 1.5, 1.7, 2, 2.2, 2.5, 2.7, 3, 3.2, 3.5, 3.7, 4, 4.2, 4.5, 4.7, 5, 5.2, 5.5, 5.7, 6, 6.2, 6.5, 6.7, 7, 7.2, 7.5, 7.7, 8, 8.2, 8.5, 8.7, 9, 9.2, 9.5, 9.7, 9.9, 10%, or any value therebetween) amino acid.

In some embodiments, the lyoprotectant composition comprises 1%-5% (e.g., 1, 1.2, 1.5, 1.7, 2, 2.2, 2.5, 2.7, 3, 3.2, 3.5, 3.7, 4, 4.2, 4.5, 4.7, 5, or any value therebetween) cyclic oligosaccharide-based polymer. In some embodiments, the lyoprotectant composition comprises 1%-3% (e.g., 1, 1.2, 1.5, 1.7, 2, 2.2, 2.5, 2.7, 3, or any value therebetween) cyclic oligosaccharide-based polymer. In some embodiments, the composition comprises 2% cyclic oligosaccharide-based polymer In some embodiments, the lyoprotectant composition comprises 4%-8% (e.g., 4, 4.2, 4.5, 4.7, 5, 5.2, 5.5, 5.7, 6, 6.2, 6.5, 6.7, 7, 7.2, 7.5, 7.7, 8%, or any value therebetween) sugar. In some embodiments, the lyoprotectant composition comprises 5%-7% (e.g., 5, 5.2, 5.5, 5.7, 6, 6.2, 6.5, 6.7, 7, or any value therebetween) sugar. In some embodiments, the composition comprises 6% sugar.

In some embodiments, the lyoprotectant composition comprises 0.2%-4% (e.g., 0.2, 0.3, 0.5, 0.7, 0.9, 1, 1.2, 1.5, 1.7, 2, 2.2, 2.5, 2.7, 3, 3.2, 3.5, 3.7, 4, or any value therebetween) amino acid. In some embodiments, the lyoprotectant composition comprises 0.3% -0.5% (e.g., 0.3, 0.4 or 0.5%) amino acid. In some embodiments, the lyoprotectant composition comprises 0.5% amino acid.

In a specific embodiment, the lyoprotectant composition comprises about 6% sucrose, about 2% gamma cyclodextrin and about 0.5% trimethylglycine.

In a specific embodiment, the lyoprotectant composition comprises about 6% sucrose, about 1% gamma cyclodextrin and about 1% trimethylglycine.

In some embodiments, the lyoprotectant composition ingredients are constituted in water or phosphate buffered saline (PBS). In some embodiments, the lyoprotectant is sterilized, optionally by filtering through a 0.2 micron filter.

Another aspect of the disclosure is directed to a composition comprising 0.3%-8% (e.g., 0.3, 0.5, 0.7, 0.9, 1, 1.2, 1.5, 1.7, 2, 2.2, 2.5, 2.7, 3, 3.2, 3.5, 3.7, 4, 4.2, 4.5, 4.7, 5, 5.2, 5.5, 5.7, 6, 6.2, 6.5, 6.7, 7, 7.2, 7.5, 7.7, 8%, or any value therebetween) cyclic oligosaccharide-based polymer, 2%-10% (e.g., 2, 2.2, 2.5, 2.7, 3, 3.2, 3.5, 3.7, 4, 4.2, 4.5, 4.7, 5, 5.2, 5.5, 5.7, 6, 6.2, 6.5, 6.7, 7, 7.2, 7.5, 7.7, 8, 8.2, 8.5, 8.7, 9, 9.2, 9.5, 9.7, 9.9, 10%, or any value therebetween) sugar, 0.2%-10% (e.g., 0.2, 0.3, 0.5, 0.7, 0.9, 1, 1.2, 1.5, 1.7, 2, 2.2, 2.5, 2.7, 3, 3.2, 3.5, 3.7, 4, 4.2, 4.5, 4.7, 5, 5.2, 5.5, 5.7, 6, 6.2, 6.5, 6.7, 7, 7.2, 7.5, 7.7, 8, 8.2, 8.5, 8.7, 9, 9.2, 9.5, 9.7, 9.9, 10%, or any value therebetween) amino acid, and a biologic drug.

In some embodiments, the composition comprises 1%-5% (e.g., 1, 1.2, 1.5, 1.7, 2, 2.2, 2.5, 2.7, 3, 3.2, 3.5, 3.7, 4, 4.2, 4.5, 4.7, 5, or any value therebetween) cyclic oligosaccharide-based polymer. In some embodiments, the composition comprises 1%-3% (e.g., 1, 1.2, 1.5, 1.7, 2, 2.2, 2.5, 2.7, 3, or any value therebetween) cyclic oligosaccharide-based polymer. In some embodiments, the composition comprises 2% cyclic oligosaccharide-based polymer In some embodiments, the composition comprises 4%-8% (e.g., 4, 4.2, 4.5, 4.7, 5, 5.2, 5.5, 5.7, 6, 6.2, 6.5, 6.7, 7, 7.2, 7.5, 7.7, 8%, or any value therebetween) sugar. In some embodiments, the composition comprises 5%-7% (e.g., 5, 5.2, 5.5, 5.7, 6, 6.2, 6.5, 6.7, 7, or any value therebetween) sugar. In some embodiments, the composition comprises 6% sugar.

In some embodiments, the composition comprises 0.2%-4% (e.g., 0.2, 0.3, 0.5, 0.7, 0.9, 1, 1.2, 1.5, 1.7, 2, 2.2, 2.5, 2.7, 3, 3.2, 3.5, 3.7, 4, or any value therebetween) amino acid. In some embodiments, the composition comprises 0.3% -0.5% (e.g., 0.3, 0.4 or 0.5%) amino acid. In some embodiments, the composition comprises 0.5% amino acid.

In a specific embodiment, the composition comprises about 6% sucrose, about 2% gamma cyclodextrin and about 0.5% trimethylglycine.

In some embodiments, the cyclic oligosaccharide-based polymer comprises an alpha cyclodextrin, beta cyclodextrin, a gamma cyclodextrin, a 2-hydroxypropyl-β-cyclodextrin, a β-cyclodextrin sulfobutylether, hydroxyethyl-β-cyclodextrin, methyl-β-cyclodextrin, dimethyl-β-cyclodextrin, carboxymethyl-β-cyclodextrin, carboxymethyl ethyl-β-cyclodextrin, diethyl-β-cyclodextrin, tri-O-alkyl-1β-cyclodextrin, glocosyl-β-cyclodextrin, maltosyl-β-cyclodextrin or any derivative thereof, and any combination thereof. In some embodiments, the cyclic oligosaccharide-based polymer comprises gamma cyclodextrin.

In some embodiments, the alpha cyclodextrin has the following chemical formula:

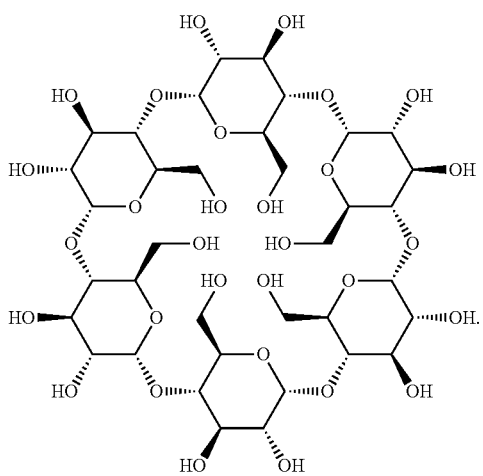 [SMILES: OC[C@H]1O[C@@H]2O[C@H]3[C@H](O)[C@@H](O)[C@@H](O[C@H]4[C@H](O)[C@@H](O)[C@@H](O[C@H]5[C@H](O)[C@@H](O)[C@@H](O[C@H]6[C@H](O)[C@@H](O)[C@@H](O[C@H]7[C@H](O)[C@@H](O)[C@@H](O[C@H]1[C@H](O)[C@H]2O)O[C@@H]7CO)O[C@@H]6CO)O[C@@H]5CO)O[C@@H]4CO)O[C@@H]3CO]

In some embodiments, the beta cyclodextrin has the following chemical formula:

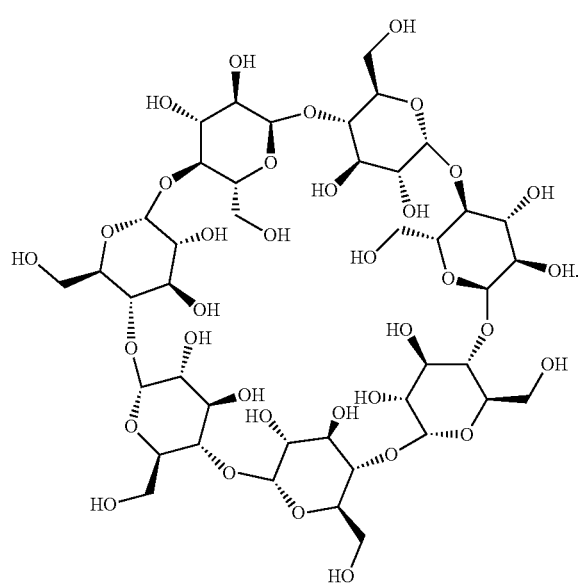 [SMILES: OC[C@H]1O[C@@H]2O[C@H]3[C@H](O)[C@@H](O)[C@@H](O[C@H]4[C@H](O)[C@@H](O)[C@@H](O[C@H]5[C@H](O)[C@@H](O)[C@@H](O[C@H]6[C@H](O)[C@@H](O)[C@@H](O[C@H]7[C@H](O)[C@@H](O)[C@@H](O[C@H]8[C@H](O)[C@@H](O)[C@@H](O[C@H]1[C@H](O)[C@H]2O)O[C@@H]8CO)O[C@@H]7CO)O[C@@H]6CO)O[C@@H]5CO)O[C@@H]4CO)O[C@@H]3CO]

In some embodiments, the gamma cyclodextrin has the following chemical formula:

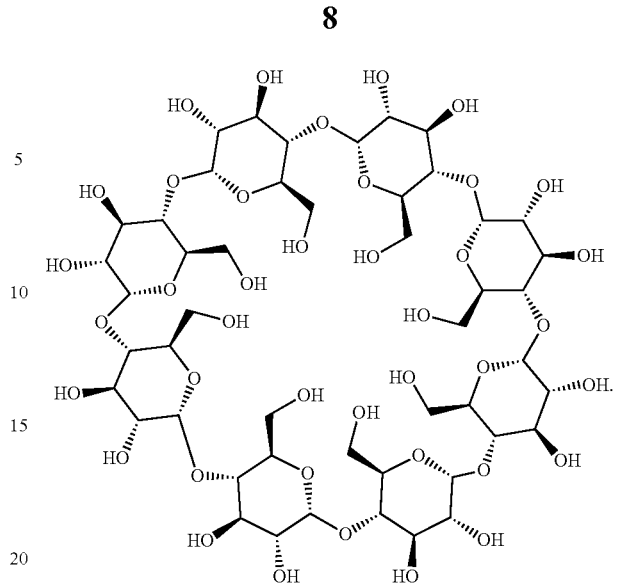

In some embodiments, the sugar comprises sucrose, mannitol, or trehalose. In some embodiments, the sugar comprises sucrose.

In some embodiments, the amino acid comprises trimethylglycine, glycine, arginine or any salts thereof.

In some embodiments, the biologic drug comprises an exosome, a liposome or a niosome. In some embodiments, the biologic drug comprises an exosome.

In some embodiments, the biologic drug (exosome, liposome or noisome) stabilized using the lyoprotectant composition of the instant disclosure during lyophilization retains at least 90% (e.g., at least 90%, 91%, 92%, 93%, 94%, 95%, 96%, 97%, 98%, 99% or more) of its structural integrity when resolubilized. In some embodiments, the lyoprotectant composition reduces agglomeration and aggregation of the biologic drug during lyophilization by at least 90% (e.g., at least 90%, 91%, 92%, 93%, 94%, 95%, 96%, 97%, 98%, 99% or more). In some embodiments, the biologic drug (exosome, liposome or noisome) stabilized using the lyoprotectant composition during lyophilization retains the bioavailability by at least 90% (e.g., at least 90%, 91%, 92%, 93%, 94%, 95%, 96%, 97%, 98%, 99% or more) when resolubilized.

In some embodiments, the biologic drug (exosome, liposome or noisome) is stabilized using the lyoprotectant composition of the instant disclosure during lyophilization, and the lyophilized composition comprising the biological drug when resolubilized has a zeta potential that is lower than −25 mV, or lower than −26 mV, or lower than −27 mV, or lower than −28 mV, or lower than −29 mV, or lower than −30 mV, or lower than −31 mV, or lower than −32 mV, or lower than −33 mV, or lower than −34 mV, or lower than −35 mV, or lower than −36 mV, or lower than −37 mV, or lower than −38 mV, or lower than −39 mV, or lower than −40 mV. In some embodiments, an exosome composition is stabilized using the lyoprotectant composition of the instant disclosure during lyophilization, and the lyophilized composition comprising the exosome when resolubilized has a zeta potential that is lower than −25 mV, or lower than −26 mV, or lower than −27 mV, or lower than −28 mV, or lower than −29 mV, or lower than −30 mV, or lower than −31 mV, or lower than −32 mV, or lower than −33 mV, or lower than −34 mV, or lower than −35 mV, or lower than −36 mV, or lower than −37 mV, or lower than −38 mV, or lower than −39 mV, or lower than −40 mV.

In some embodiments, the biologic drug (exosome, liposome or noisome) is stabilized using the lyoprotectant composition of the instant disclosure during lyophilization, and the lyophilized composition comprising the biological drug when resolubilized has a zeta potential that is no more than 10 mV, no more than 9 mV, no more than 8 mV, no more than 7 mV, no more than 6 mV, no more than 5 mV, no more than 4 mV, no more than 3 mV, no more than 2 mV, or no more than 1 mV, higher than the zeta potential of a corresponding non-lyophilized composition comprising the biological drug. In some embodiments, an exosome composition is stabilized using the lyoprotectant composition of the instant disclosure during lyophilization, and the lyophilized composition comprising the exosome when resolubilized has a zeta potential that is no more than 10 mV, no more than 9 mV, no more than 8 mV, no more than 7 mV, no more than 6 mV, no more than 5 mV, no more than 4 mV, no more than 3 mV, no more than 2 mV, or no more than 1 mV, higher than the zeta potential of a corresponding non-lyophilized composition comprising the exosome.

Methods for Stabilizing a Biologic Drug

Another aspect of the disclosure is directed to a method for stabilizing a biologic drug during lyophilization comprising mixing the biologic drug with a lyoprotectant blend before lyophilization, wherein the lyoprotectant blend comprises: 0.3%-8% (e.g., 0.3, 0.5, 0.7, 0.9, 1, 1.2, 1.5, 1.7, 2, 2.2, 2.5, 2.7, 3, 3.2, 3.5, 3.7, 4, 4.2, 4.5, 4.7, 5, 5.2, 5.5, 5.7, 6, 6.2, 6.5, 6.7, 7, 7.2, 7.5, 7.7, 8%, or any value therebetween) cyclic oligosaccharide-based polymer, 2%-10% (e.g., 2, 2.2, 2.5, 2.7, 3, 3.2, 3.5, 3.7, 4, 4.2, 4.5, 4.7, 5, 5.2, 5.5, 5.7, 6, 6.2, 6.5, 6.7, 7, 7.2, 7.5, 7.7, or 8, 8.2, 8.5, 8.7, 9, 9.2, 9.5, 9.7, 9.9, 10%, or any value therebetween) sugar, and 0.2%-10% (e.g., 0.2, 0.3, 0.5, 0.7, 0.9, 1, 1.2, 1.5, 1.7, 2, 2.2, 2.5, 2.7, 3, 3.2, 3.5, 3.7, 4, 4.2, 4.5, 4.7, 5, 5.2, 5.5, 5.7, 6, 6.2, 6.5, 6.7, 7, 7.2, 7.5, 7.7, 8, 8.2, 8.5, 8.7, 9, 9.2, 9.5, 9.7, 9.9, 10%, or any value therebetween) amino acid.

Another aspect of the disclosure is directed to a method for stabilizing a biologic drug during lyophilization comprising mixing the biologic drug with a lyoprotectant blend before lyophilization, wherein the lyoprotectant blend comprises: 0.3%-8% (e.g., 0.3, 0.5, 0.7, 0.9, 1, 1.2, 1.5, 1.7, 2, 2.2, 2.5, 2.7, 3, 3.2, 3.5, 3.7, 4, 4.2, 4.5, 4.7, 5, 5.2, 5.5, 5.7, 6, 6.2, 6.5, 6.7, 7, 7.2, 7.5, 7.7, 8%, or any value therebetween) cyclic oligosaccharide-based polymer, 2%-10% (e.g., 2, 2.2, 2.5, 2.7, 3, 3.2, 3.5, 3.7, 4, 4.2, 4.5, 4.7, 5, 5.2, 5.5, 5.7, 6, 6.2, 6.5, 6.7, 7, 7.2, 7.5, 7.7, 8, 8.2, 8.5, 8.7, 9, 9.2, 9.5, 9.7, 9.9, 10%, or any value therebetween) sugar, 0.2%-10% (e.g., 0.2, 0.3, 0.5, 0.7, 0.9, 1, 1.2, 1.5, 1.7, 2, 2.2, 2.5, 2.7, 3, 3.2, 3.5, 3.7, 4, 4.2, 4.5, 4.7, 5, 5.2, 5.5, 5.7, 6, 6.2, 6.5, 6.7, 7, 7.2, 7.5, 7.7, 8, 8.2, 8.5, 8.7, 9, 9.2, 9.5, 9.7, 9.9, 10%, or any value therebetween) amino acid, and a biologic drug.

In some embodiments, the lyoprotectant blend comprises 1%-5% (e.g., 1, 1.2, 1.5, 1.7, 2, 2.2, 2.5, 2.7, 3, 3.2, 3.5, 3.7, 4, 4.2, 4.5, 4.7, 5, or any value therebetween) cyclic oligosaccharide-based polymer. In some embodiments, the lyoprotectant blend comprises 1%-3% (e.g., 1, 1.2, 1.5, 1.7, 2, 2.2, 2.5, 2.7, 3, or any value therebetween) cyclic oligosaccharide-based polymer. In some embodiments, the lyoprotectant blend comprises 2% cyclic oligosaccharide-based polymer In some embodiments, the lyoprotectant blend comprises 4%-8% (e.g., 4, 4.2, 4.5, 4.7, 5, 5.2, 5.5, 5.7, 6, 6.2, 6.5, 6.7, 7, 7.2, 7.5, 7.7, 8%, or any value therebetween) sugar. In some embodiments, the lyoprotectant blend comprises 5%-7% (e.g., 5, 5.2, 5.5, 5.7, 6, 6.2, 6.5, 6.7, 7, or any value therebetween) sugar. In some embodiments, the lyoprotectant blend comprises 6% sugar.

In some embodiments, the lyoprotectant blend comprises 0.2%-4% (e.g., 0.2, 0.3, 0.5, 0.7, 0.9, 1, 1.2, 1.5, 1.7, 2, 2.2, 2.5, 2.7, 3, 3.2, 3.5, 3.7, 4, or any value therebetween) amino acid. In some embodiments, the lyoprotectant blend comprises 0.3% -0.5% (e.g., 0.3, 0.4 or 0.5%) amino acid. In some embodiments, the composition comprises 0.5% amino acid.

In some embodiments, the cyclic oligosaccharide-based polymer comprises comprises an alpha cyclodextrin, beta cyclodextrin, a gamma cyclodextrin, a 2-hydroxypropyl-β-cyclodextrin, a β-cyclodextrin sulfobutylether, hydroxyethyl-β-cyclodextrin, methyl-β-cyclodextrin, dimethyl-β-cyclodextrin, carboxymethyl-β-cyclodextrin, carboxymethyl ethyl-β-cyclodextrin, diethyl-β-cyclodextrin, tri-O-alkyl-1β-cyclodextrin, glocosyl-β-cyclodextrin, maltosyl-β-cyclodextrin or any derivative thereof, and any combination thereof. In some embodiments, the cyclic oligosaccharide-based polymer comprises gamma cyclodextrin.

In some embodiments, the alpha cyclodextrin has the following chemical formula:

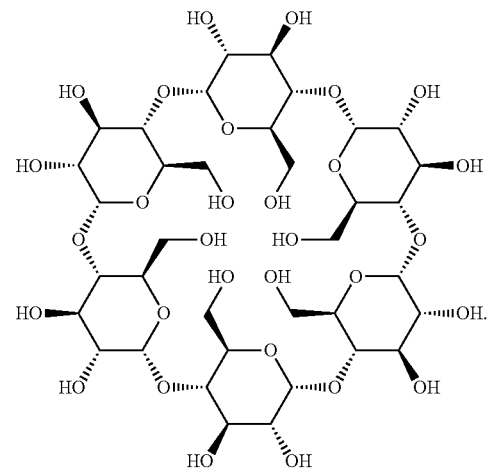 [SMILES: OC[C@H]1O[C@@H]2O[C@H]3[C@H](O)[C@@H](O)[C@@H](O[C@H]4[C@H](O)[C@@H](O)[C@@H](O[C@H]5[C@H](O)[C@@H](O)[C@@H](O[C@H]6[C@H](O)[C@@H](O)[C@@H](O[C@H]7[C@H](O)[C@@H](O)[C@@H](O[C@H]1[C@H](O)[C@H]2O)O[C@@H]7CO)O[C@@H]6CO)O[C@@H]5CO)O[C@@H]4CO)O[C@@H]3CO]

In some embodiments, the beta cyclodextrin has the following chemical formula:

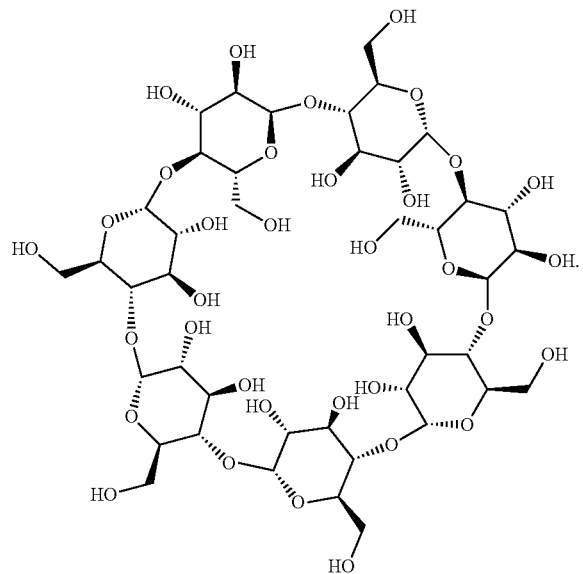 [SMILES: OC[C@H]1O[C@@H]2O[C@H]3[C@H](O)[C@@H](O)[C@@H](O[C@H]4[C@H](O)[C@@H](O)[C@@H](O[C@H]5[C@H](O)[C@@H](O)[C@@H](O[C@H]6[C@H](O)[C@@H](O)[C@@H](O[C@H]7[C@H](O)[C@@H](O)[C@@H](O[C@H]8[C@H](O)[C@@H](O)[C@@H](O[C@H]1[C@H](O)[C@H]2O)O[C@@H]8CO)O[C@@H]7CO)O[C@@H]6CO)O[C@@H]5CO)O[C@@H]4CO)O[C@@H]3CO]

In some embodiments, the gamma cyclodextrin has the following chemical formula:

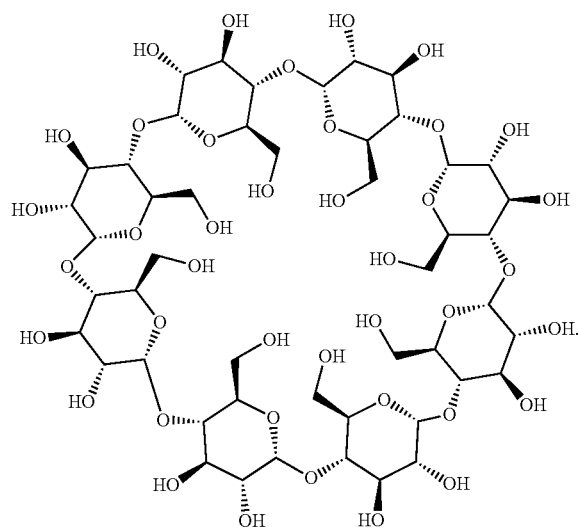 [SMILES: OC[C@H]1O[C@@H]2O[C@H]3[C@H](O)[C@@H](O)[C@@H](O[C@H]4[C@H](O)[C@@H](O)[C@@H](O[C@H]5[C@H](O)[C@@H](O)[C@@H](O[C@H]6[C@H](O)[C@@H](O)[C@@H](O[C@H]7[C@H](O)[C@@H](O)[C@@H](O[C@H]8[C@H](O)[C@@H](O)[C@@H](O[C@H]9[C@H](O)[C@@H](O)[C@@H](O[C@H]1[C@H](O)[C@H]2O)O[C@@H]9CO)O[C@@H]8CO)O[C@@H]7CO)O[C@@H]6CO)O[C@@H]5CO)O[C@@H]4CO)O[C@@H]3CO]

In some embodiments, the sugar comprises sucrose, mannitol, or trehalose. In some embodiments, the sugar comprises sucrose.

In some embodiments, the amino acid comprises trimethylglycine, glycine, arginine or any salts thereof.

In some embodiments, the cyclic oligosaccharide-based polymer comprises gamma cyclodextrin, wherein the sugar comprises sucrose, wherein the amino acid comprises trimethylglycine, wherein the biologic drug comprises an exosome.

In a specific embodiment, the lyoprotectant blend comprises about 6% sucrose, about 1% gamma cyclodextrin and about 1% trimethylglycine and an exosome.

In some embodiments, the biologic drug comprises an exosome, a liposome or a niosome. In some embodiments, the biologic drug comprises an exosome.

In some embodiments, the biologic drug (exosome, liposome or niosome) stabilized by the method during lyophilization retains at least 90% (e.g., at least 90%, 91%, 92%, 93%, 94%, 95%, 96%, 97%, 98%, 99% or more) of its structural integrity when resolubilized. In some embodiments, lyoprotectant blend reduces agglomeration and aggregation of the biologic drug during lyophilization by at least 90% (e.g., at least 90%, 91%, 92%, 93%, 94%, 95%, 96%, 97%, 98%, 99% or more). In some embodiments, the biologic drug (exosome, liposome or niosome) stabilized by the method during lyophilization retains the bioavailability by at least 90% (e.g., at least 90%, 91%, 92%, 93%, 94%, 95%, 96%, 97%, 98%, 99% or more) when resolubilized.

In some embodiments, the biologic drug (exosome, liposome or niosome) is stabilized by the method of the instant disclosure during lyophilization, and the lyophilized composition comprising the biological drug when resolubilized has a zeta potential that is lower than −25 mV, or lower than −26 mV, or lower than −27 mV, or lower than −28 mV, or lower than −29 mV, or lower than −30 mV, or lower than −31 mV, or lower than −32 mV, or lower than −33 mV, or lower than −34 mV, or lower than −35 mV, or lower than −36 mV, or lower than −37 mV, or lower than −38 mV, or lower than −39 mV, or lower than −40 mV. In some embodiments, an exosome composition is stabilized by the method of the instant disclosure during lyophilization, and the lyophilized composition comprising the exosome when resolubilized has a zeta potential that is lower than −25 mV, or lower than −26 mV, or lower than −27 mV, or lower than −28 mV, or lower than −29 mV, or lower than −30 mV, or lower than −31 mV, or lower than −32 mV, or lower than −33 mV, or lower than −34 mV, or lower than −35 mV, or lower than −36 mV, or lower than −37 mV, or lower than −38 mV, or lower than −39 mV, or lower than −40 mV.

In some embodiments, the biologic drug (exosome, liposome or niosome) is stabilized by the method of the instant disclosure during lyophilization, and the lyophilized composition comprising the biological drug when resolubilized has a zeta potential that is no more than 10 mV, no more than 9 mV, no more than 8 mV, no more than 7 mV, no more than 6 mV, no more than 5 mV, no more than 4 mV, no more than 3 mV, no more than 2 mV, or no more than 1 mV, higher than the zeta potential of a corresponding non-lyophilized composition comprising the biological drug. In some embodiments, an exosome composition is stabilized by the method of the instant disclosure during lyophilization, and the lyophilized composition comprising the exosome when resolubilized has a zeta potential that is no more than 10 mV, no more than 9 mV, no more than 8 mV, no more than 7 mV, no more than 6 mV, no more than 5 mV, no more than 4 mV, no more than 3 mV, no more than 2 mV, or no more than 1 mV, higher than the zeta potential of a corresponding non-lyophilized composition comprising the exosome.

Examples

Example 1: Materials and Methods

In almost every field of biomedical research, analysis of EVs is required. Hence, specific issues arise when working with these entities, whose size and amount often make them difficult to obtain as relatively pure preparations, and to characterize properly. The International Society for Extracellular Vesicles (ISEV) proposed Minimal Information for Studies of Extracellular Vesicles ("MISEV") guidelines for the field.

Presented herein is a thorough and detailed characterization of the EV preparations lyophilized using the lyoprotectant compositions of the instant disclosure using the MISEV guidelines as reference.

Samples. Sample A: Lyophilized exosome sample in 6% sucrose, 2% gamma cyclodextrin; Sample B: Lyophilized exosome sample in 5% mannitol; Sample C: non-lyophilized liquid control exosome sample; Sample E: Lyophilized exosome sample in 4% sucrose and 1% gamma cyclodextrin; Sample F: Lyophilized exosome sample in 6% sucrose, 1% gamma cyclodextrin and 1% trimethylglycine (TMG); 62822-02: Control liquid non-lyophilized exosome composition (different concentration than Sample C); 62822-01: lyophilized liquid control exosome sample in 5% Mannitol.

EV Enrichment Ultracentrifugation. Samples were ultracentrifuged in an Optima L-90K ultracentrifuge (Beckman) for 70 minutes at 4° C. at 34,000 rpm using a Beckman SW 55 Ti swing bucket rotor (k-factor 45 at maximum speed). Polycarbonate tubes (Beckman catalogue number 349622) were filled up to 2.0 mL. Relative centrifugation force (RCF) span from 140,100 g (max radius 108.5 mm) to 109,239 g (average radius 84.6 mm). Pellets were resolubilized 50 µL of 0.1 µm filtered PBS.

Protein assay, Gel electrophoresis and Western blot. Protein quantification was performed by Qubit Protein assay (ThermoFisher Scientific; Catalogue number Q33211). One mL of sample was precipitated by 20% (v/v) trichloracetic acid (TCA) and 0.08% (w/v) sodium deoxycholate (DOC). Briefly, 250 µL of 100% (v/v) TCA+0.4% (w/v) DOC was added to 1.0 mL of EV solution, vortexed and incubated in ice for 30 minutes. Samples were then centrifuged at max speed (14,000 rpm; RCF 18,000 g) for 30 minutes at 2° C. Supernatant was discarded and the pellet was added 800 µL 100% (v/v) acetone and incubated at −20° C. overnight and then centrifuged max speed (14,000 rpm; RCF 18,000 g) for 30 minutes at 2° C. Supernatants were discarded and the pellets dried in the fume hood for 10 minute before resuspending in the electrophoresis solubilization buffer (ESB): 6 M urea (BioRad Laboratories), 2 M thiourea, 5% (w/v) sodium dodecyl sulphate (SDS) (BioRad Laboratories), 40 mM Tris-HCl, pH 6.8, 0.5 mm ethylenediaminetetraacetic acid (EDTA) (BioRad Laboratories), 20% (v/v) glycerol and 50 mM dithiothreitol (DTT) (BioRad Laboratories). Samples were denaturized overnight at room temperature (RT). Proteins were separated by hand cast SDS-PAGE gradient gels (Resolving gel T=5-20% (w/v); C=2.6%; Stacking gel T=3.5% (w/v); C=2.6%) in 25 mM Tris (BioRad Laboratories), 192 mM glycine (BioRad Laboratories) and 0.1% (w/v) SDS (Bio-Rad Laboratories) buffer and either stained with colloidal Coomassie G-250 or transferred onto a 0.45 µm nitrocellulose membrane (Amersham Protean 0.45 µm NC, Life Sciences) in a wet transfer system buffer made of 25 mM Tris, 192 mM glycine and 20% (v/v) methanol for 3 hours at 200 mA per gel in ice bath. Nitrocellulose membranes were saturated with Odyssey blocking buffer (Li-Cor Biosciences) and incubated in 0.5 µg/mL rabbit anti tumor susceptibility gene 101 protein (TSG101) (Code T5701) (Sigma-Aldrich); 1.0 µg/mL biotinylated mouse anti CD9 (clone HI9a), CD63 (clone H5C6) and CD81(clon TAPA-1; Biolegend CD9 catalogue number 312112; CD63 catalogue number 353017; CD81 catalogue number 349514); 1.0 µg/mL mouse anti calnexin (clone E-10) (Santa Cruz catalogue number SC-46669), 1.0 µg/mL mouse anti Syntenin-1 (cloneC-3) (Santa Cruz catalogue number sc-515538); 1.0 µg/mL mouse anti ALIX (clone 1Al2) (Santa Cruz catalogue number sc-53540); 1.0 µg/mL mouse anti CD9 (clone C-4) (Santa Cruz catalogue number sc-13118), 1.0 µg/mL mouse anti CD63 (clone MX49.129.5) (Santa Cruz catalogue number sc-5275), 1.0 µg/mL mouse anti CD81 (clone B-11) (Santa Cruz catalogue number sc-166029), and 1.0 µg/mL mouse anti LL-37 (Clone D-5) (Santa Cruz catalogue number SC-166770) overnight at room temperature (RT) in the Odyssey blocking buffer diluted 1:1 with in house PBS (10 mM sodium phosphate dibasic, 1.8 mM potassium phosphate monobasic, 137 mM sodium chloride, 2.7 mM potassium chloride) and 0.15% (v/v) Tween-20. After 3×10 minute washes in PBS-Tween (0.15%, v/v), membranes were incubated with goat anti mouse (code 925-68070 and/or 925-32210), goat anti rabbit (code 925-68071 and/or 925-32211) and donkey anti goat (code 925-68074) either red (displayed in red colour excitation 680 nm, emission 700 nm) or infrared (displayed in green colour excitation 780 nm, emission 800 nm) dye-coupled secondary antibody 0.1 µg/mL (Li-Cor Biosciences) in an Odyssey blocking solution diluted at 1:1 with PBS and 0.15% (v/v) Tween-20; 1hour at RT. Acquisition of the fluorescent signal was performed by Odyssey infrared imaging system with resolution set at 169 µm (Li-Cor Biosciences). Image studio software version 2.1 (Li-Cor Biosciences) was used to analyse and export images.

Sample preparation for mass spectrometry (MS). One ml of TCA precipitated pellet was resolubilized in 100 µL of 0.1% (w/v) of SDS. Ten µg equivalent volume of sample was diluted to 100 µL of 0.1 µm filtered PBS and delipidated by chloroform methanol. Briefly, 400 µL of 100% (v/v) methanol was added to the sample, vortexed and centrifuged for 10 seconds at 9000 g. Two hundred µL of chloroform were added, vigorously vortexed and centrifuged for 10 seconds at 9000 g. Three hundred µL of deionized water was added, mixed vigorously and centrifuged for 5 minutes at 9000 g. The aqueous upper phase was discarded and the interface protein layer was precipitated by adding 300 µL of 100% (v/v) methanol and centrifuged for 30 minutes at max speed.

Nanoparticle Tracking Analysis (NTA). NTA was performed using the ZetaView PMX-220 Twin (Particle Metrix) configured with a 488 nm and 640 nm lasers with a long wave-pass (LWP) cut-off filters (500 nm and 660 nm respectively) and a sensitive CMOS camera 640×480 pixels. Samples were diluted in 2 mL of 0.1 µm filtered (Minisart® high flow hydrophilic 0.1 µm syringe filter Sartorious) deionized water (DI 18 MΩ/cm) to obtain a particle concentration between $1\times10^7$ and $1\times10^8$ particles/mL (50-200 particles). The instrument was set to a sensitivity of 75, a shutter speed of 75 and a frame rate of 30 frames per second (fps). Each sample was measured at 11 different positions throughout the cell, with 1 cycle of reading at each position to have a minimum of 1000 traces. If the number of traces was below 1000 counts some additional sample was flushed inside the cell and the acquisition repeated. Post-acquisition parameters were set to a minimum brightness of 20, a maximum size area of 1000 pixels, a minimum size area of 10 pixels and tracelength of 15 frames. Automated cell quality control was checked using high quality deionized water (DI). Camera alignment and focus optimization was performed using polystyrene NanosphereTM 100 nm size standard beads (Thermo Scientific catalogue number 3100A). Data analysis was performed with ZetaView 8.05.14 software provided by the manufacturer. Automated report of the particles recording across the 11 positions were manually checked and any outlier position was removed to calculate particle concentration and distribution.

Microfluidic resistive pulse sensing (MRPS). Particle number concentrations and size distributions were measured by microfluidic resistive pulse sensing (MRPS) using the Spectradyne nCS1 instrument (Spectradyne, Torrence, CA) equipped with a C400 (65-400 nm) and C900 (135-900 nm) polydimethylsiloxane cartridges to cover a size range of approximately 65-900 nm in vesicle diameters. The microfluidic system was primed with a solution of 1% Tween 20 (v/v) phosphate buffer solution (PBS) filtered with 0.1 µm syringe filter (Minisart® PES catalogue number 16553K, Sartorious). Priming is the process of generating an appropriate ionic electric current in the system and wetting all channels of the cartridge. Samples were diluted with a solution of 1% Tween-20 (v/v) in PBS filtered with 0.02 µm Whatman™ Anotop™ syringe filter (Cytiva catalogue number 6809-3002). All samples were diluted such that the resulting particle concentrations fell within the operational range of each cartridge specified by the manufacturer. Five uL of diluted sample was loaded in the cartridge. Ten seconds acquisitions were performed in continuous mode using the auto-analysis engine interface that automatically processed the raw data with an acquisition stop point set on 2.0 percent error corresponding to 2500 particles. The auto-analysis engine setting was based on the manufacture standard parameters: peak detection threshold of 3 times the standard deviation of the baseline noise (3σ) and fit-width 4 times more of the mean transit time of high signal-to-noise particle events. Data analysis was performed with the nCS1

Data Viewer (Version 2.5.0.249; Spectradyne). The acquisition of the buffer only was used to subtract the background noise from the sample and work out the particle concentration.

Concentration Spectral Density (CSD) represents the number of particles per unit sample volume (measured in mL) per unit particle diameter (measured in nm). By including "per unit particle diameter" part, one creates a histogram that is already normalized by the bin size, meaning that this histogram can be easily compared with other histograms. If the absolute concentration of particles are to be calculated in a range of particle diameters, the desired range is integrated (in other words, summed), generating a size histogram with the desired bin widths. That summed result would be a histogram of the number of particles per ml for the chosen bin size.

Single particle interferometric reflectance imaging sensor (SP-IRIS). Tetraspanin CD9, CD63 and CD81 distribution were analyzed using the ExoViewR100 platform using the tetraspanin ExoView kits (EV-TETRA-C, NanoView Biosciences, Boston, MA, USA) following the kit assay protocol. Briefly, EV ultracentrifugation pellets were diluted 100 times with the incubation solution II. Sixty five µL of the dilute samples were placed on top of the chips inside a Falcon 24-well cell culture plate, flat bottom (Fisher Scientific Catalogue number 08-772-1) for the capture of EV carrying CD9 (Clone HI9a), CD63 (Clone H5C6), CD81antigen (Clone JS-81) and mouse isotype IgG (Clone MOPC-21). After 16 h incubation at room temperature chips were washed 3 times with 1 X solution A for 3 minutes on ELISA microplate orbital shaker at 500 rpm (Fisherbrand™ Fisher Scientific Catalogue number 88-861-023). Chips were then incubated with an antibody cocktail made of 0.6 µL anti-human CD81+conjugated with Alexfluor 555, 0.6 µL CD63+conjugated with Alexfluor 647, and 0.6 µL CD9+ conjugated with Alexfluor 488 in 300 µL of blocking solution for 1 h at RT on orbital shaker at 500 rpm. Chips were washed 1 time with 1X solution A, 3 times with 1X resolution B and 1 time with DI water respectively for 3 minutes at 500 rpm. After careful drying the chips, image acquisition from each chip was carried out using the ExoView® R100 platform, and the data were analyzed by the ExoView Analyzer software version 3.2 (NanoView Biosciences). The images of the acquisition were visually inspected and all the artifacts onto the spots were manually removed from the analysis. Non-specific binding was checked on the mouse isotype control IgG spots. The cut off was manually established for each chip to exclude most of the signal (>90%) captured on the isotype control.

Microfluidic resistive pulse sensing (MRPS) Electrical Sensing Zone (ESZ), also known as microfluidic resistive pulse sensing (MRPS), is a non-light-based technique for sizing and counting of particles in the nm- and µm-size range.

ESZ/MRPS works by applying an electrical field between opposite sides of an orifice. Particles suspended in a conductive electrolyte solution are aspirated through the orifice and, upon passage, increase the electrical resistance proportional to the volume of their non-conductive part (Coulter principle). Size determination is based on calibration with spherical sizing-standards and provides therefore an equivalent spherical diameter of the analyzed particles. Depending on the system and set-up, particles from about 50 nm up to 1 mm can be measured. In the instant case, a Spectradyne system was used in the MRPS analysis.

Single particle interferometric reflectance imaging sensor (SP-IRIS). Single-particle interferometric reflectance imaging sensing (SP-IRIS) assay was carried out using the Exoview™ platform as described in Deng, Fengyan, et al. ("Single-particle interferometric reflectance imaging characterization of individual extracellular vesicles and population dynamics." Journal of visualized experiments: JoVE 179 (2022)), which is incorporated herein in its entirety. Briefly, SP-IRIS captures particles (e.g., EVs) onto a chip with antibodies. These antibodies include mouse anti CD9 clone (HI9a), mouse anti CD63 clone (clone H5C6), and mouse anti CD81 clone (clone JS-81). These are the same clones of antibodies from Biolegend that are used in the Western blots. Anti-CD9 cross-reacts with bovine CD9 according to the Exoview Kit assay protocol. This assay works similarly to an ELISA assay, with a capture antibody and a detection antibody forming a sandwich. However, the concentration cannot be extrapolated since there is no standard curve. Accordingly, this assay provides relative quantification when the measurement is performed in the linear range of 100-5000 particle counts. Instead, SP-IRIS is best used for characterizing single particles and understanding ratios within populations. SP-IRIS technique can be used for multi-level and comprehensive measurements for the analysis of EV size, EV count, EV phenotype, and biomarker colocalization.

Example 2: Characterizing Extracellular Vesicle (EV) Preparations in Lyoprotectant Compositions The objective of the instant study was to provide a full characterization of the EV preparations and to identify similarities and differences between the non-lyophilized control exosome samples (62822-02 and Sample C, which only differed in concentration) and the lyophilized exosome preparations (62822-01; Samples A, B, E and F).

Gel electrophoresis was used to evaluate the protein pattern in exosome samples, both non-lyophilized control samples and lyophilized samples in differed lyoprotectant blends as described herein (FIGS. 1A-1C). As a positive control, urinary extracellular vesicles were used. A notable feature of all of the EV samples (Samples 628222-02, A-F) is the presence of a band centered around 67 kDa, which is consistent with the molecular weight of albumin. When Sample B (*) was placed among samples without reducing reagent (DTT) an apparent shift in the molecular weight was observed (FIG. 1C). There are 35 cysteines in albumin, 34 of which are in disulfide bonds, while only one is free in position 34. In the presence of DTT, albumin has a higher degree of unfolding that results in a higher apparent molecular weight than samples without DTT. The protein pattern is very consistent and similar among samples (Sample A-C), with albumin at 67 kDa being dominant. It is interesting to observe an enrichment of peptides smaller than 10 kDa in the ultracentrifugation pellets (UC). These samples were ultracentrifuged to increase the EV concentration for the electron microscopy analysis carried out at the Electron Microscopy Resource Lab at the University of Pennsylvania.

The quality control of the sample submitted to the proteomic core facility for comprehensive characterization of the proteins present in the EV preparation is shown in FIG. 2. For the LC-MS analysis, the sample was delipidated in chloroform and methanol (Chl/Meth) to remove excess lipids that might interfere with the reduction-alkylation and trypsin digestion steps. This sample is in the care of the Proteomic Core Facility at the Children's Hospital of Philadelphia (CHOP).

Some particles were observed with morphology consistent with EV using cryogenic electron microscopy (Cryo-EM), including a double phospholipid bilayer. Additional small structures (10-30 nm) as well as some amorphous material were detected.

As a result of electrophoresis, a very complex protein composition was observed, and the effect of the protein corona should be considered, particularly when referring to lyophilization-resolubilization and freezing-thawing cycles. Changes in PSD and particle number can be attributed to changes in the composition of the soft corona. Changes in the refractive index of the particle, as well as the structure of the particle+the protein corona can play a role in this process. Zeta potential changes can be explained for the same reasons. Similarly, the protein corona can play a role in all particle analysis techniques. In any immune-based assay, antigen masking or steric hindrance may affect antibody affinity for the antigen Nanoparticle tracking analysis (NTA). Table 1 summarizes the results for particle size, concentration, and zeta potential. Zeta potential reflects the surface charge of certain particles, which is related to their stability due to electrostatic forces. When the zeta potential is higher than absolute 25 mV (i.e., higher than 25 m, or lower than −25 mV) the suspension is considered stable and less likely to aggregate.

Sample C is the non-lyophilized reference sample. There was a higher concentration and a shift in the median of 10-20 nm for all lyophilized samples. In spite of changes in conductivity and dilution of the sample, the zeta potential exhibited a much higher degree of variability from preparation to preparation.

TABLE 1

Particle size distribution (PSD) expressed as Median (X50), Particle concentration, Zeta potential and conductivity are the average of the value obtained from each acquisition

| Sample | Median X50 (nm) | Particle concentration (Particles/mL) | Zeta Potential (mV) | Conductivity sensed (µS/cm) |
|---|---|---|---|---|
| Sample A Oct. 21, 2022 | 196.7 | $5.58 \times 10^8$ | −31.02 | 823.20 |
| Sample B Oct. 21, 2022 | 179.6 | $4.10 \times 10^8$ | −27.52 | 732.62 |
| Sample C Nov. 17, 2022 | 165.6 | $7.43 \times 10^7$ | −40.44 | 1341.61 |
| Sample E Nov. 17, 2022 | 198.25 | $5.05 \times 10^8$ | −30.47 | 1608.96 |
| Sample F Nov. 17, 2022 | 187.2 | $4.25 \times 10^8$ | −36.91 | 1068.49 |

In the instant case, the MRPS analysis showed a larger number of particles particularly in the small range (65-100 nm) than the NTA. The particle side distribution followed a power-law distribution (FIGS. 3A-3D) similar to what has been estimated by electron microscopy for biological samples. In addition, Sample F showed the highest absolute Zeta potential after Sample C (the non-lyophilized liquid control sample), indicating that Sample F protected the integrity and shape of the exosomes and also prevented the exosomes from aggregation during lyophilization and reconstitution (see, Table 1).

TABLE 2

Particle concentrations were measured with C400 (65-400 nm) and C900 (130-900 nm) cartridges. Samples 62822-02 and 62822-01 were measured with TS400 (65-400 nm) and C900 (130-900 nm) cartridges.

| Sample | Particle concentration C400 (Particles/mL) | Particle concentration C900 (Particles/mL) |
|---|---|---|
| 62822-02 Jul. 27, 2022 | $1.22 \times 10^{10}$ | $2.13 \times 10^7$ |
| 62822-01 Jul. 27, 2022 | $8.48 \times 10^8$ | $6.21 \times 10^7$ |

TABLE 2-continued

Particle concentrations were measured with C400 (65-400 nm) and C900 (130-900 nm) cartridges. Samples 62822-02 and 62822-01 were measured with TS400 (65-400 nm) and C900 (130-900 nm) cartridges.

| Sample | Particle concentration C400 (Particles/mL) | Particle concentration C900 (Particles/mL) |
|---|---|---|
| Sample A Sep. 06, 2022 | $3.54 \times 10^{10}$ | $2.28 \times 10^8$ |
| Sample B Nov. 17, 2022 | $3.24 \times 10^9$ | $1.34 \times 10^8$ |
| Sample C Nov. 17, 2022 | $1.38 \times 10^9$ | $3.44 \times 10^7$ |
| Sample E Nov. 17, 2022 | $1.36 \times 10^{10}$ | $3.81 \times 10^8$ |
| Sample F Nov. 17, 2022 | $8.69 \times 10^9$ | $4.16 \times 10^8$ |

In general, the results of the particle concentration indicate the same trend as that described in the NTA section. It is particularly evident and substantial that the particle concentrations of the lyophilized samples A, B, E and F are higher when measured using the C900 cartridge (detection range 130 to 900 nm).

The MRPS results were consistent with those of the NTA. Due to the lower limit of detection (LOD) of the C400 cartridge, more particles were not detected. Furthermore, the manufacturer (Spectradyne) recommended dilution of the sample in 1% Tween 20 buffer in order to avoid clogging the nanopores. Therefore, the increased particle counts determined by MRPS for the same samples may be a result of an increase in particle polydispersity or an artifactual production of small particles. This may occur when EV complexes or aggregates are disrupted by detergent. It has been shown in several studies that Tween 20 is a mild detergent that does not adversely affect the integrity of EVs even at high concentrations (1%).

Figure 4A:
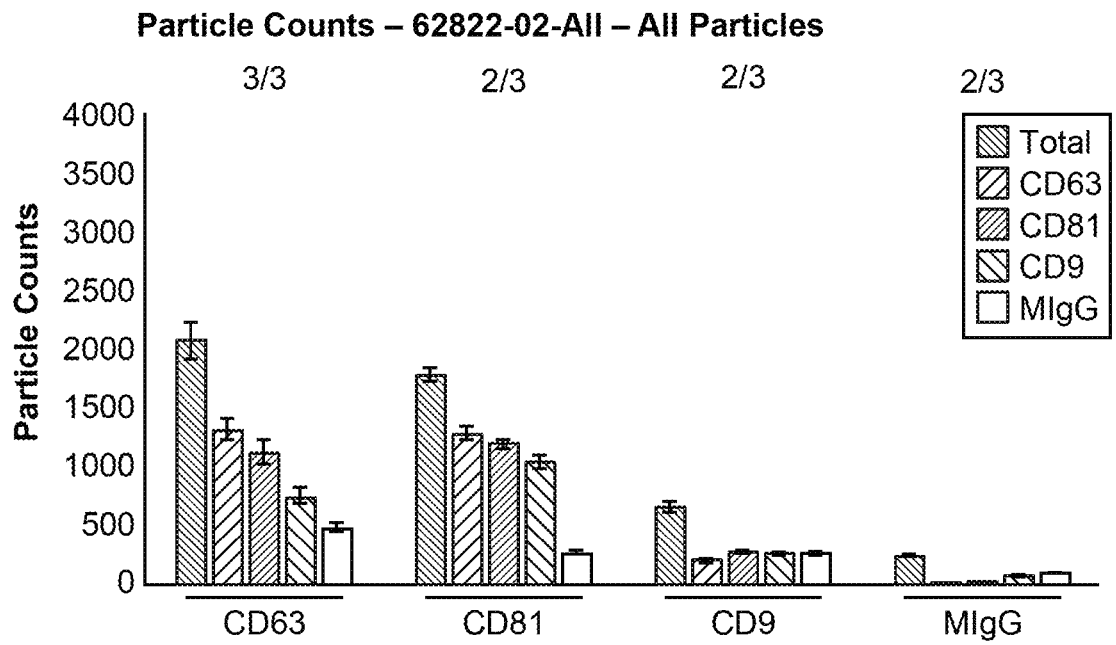
Figure 4B:
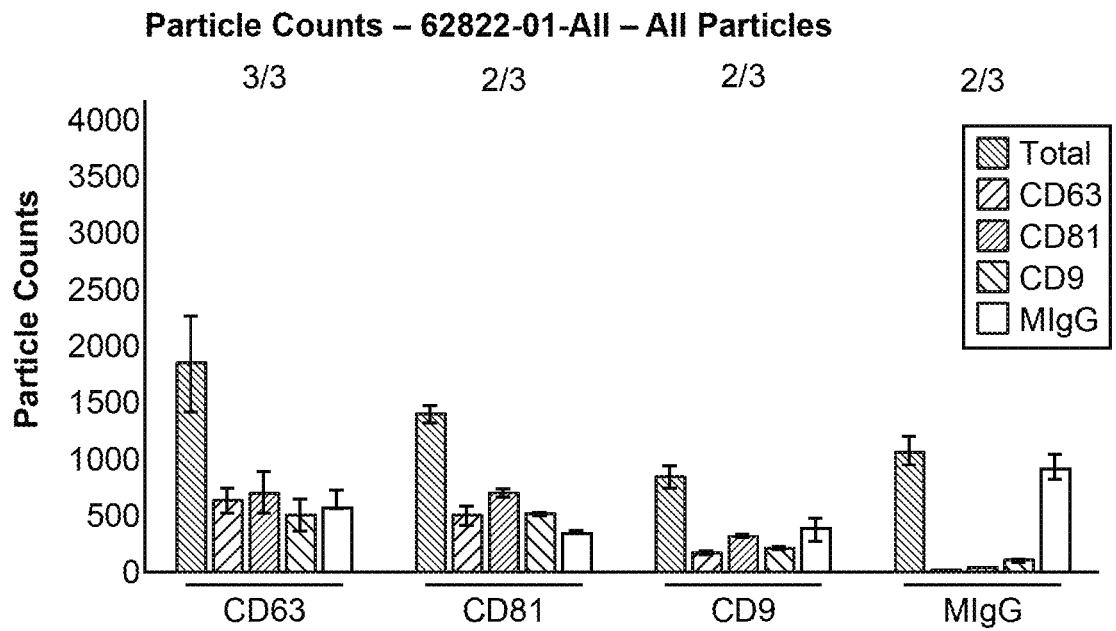
Figure 4C:
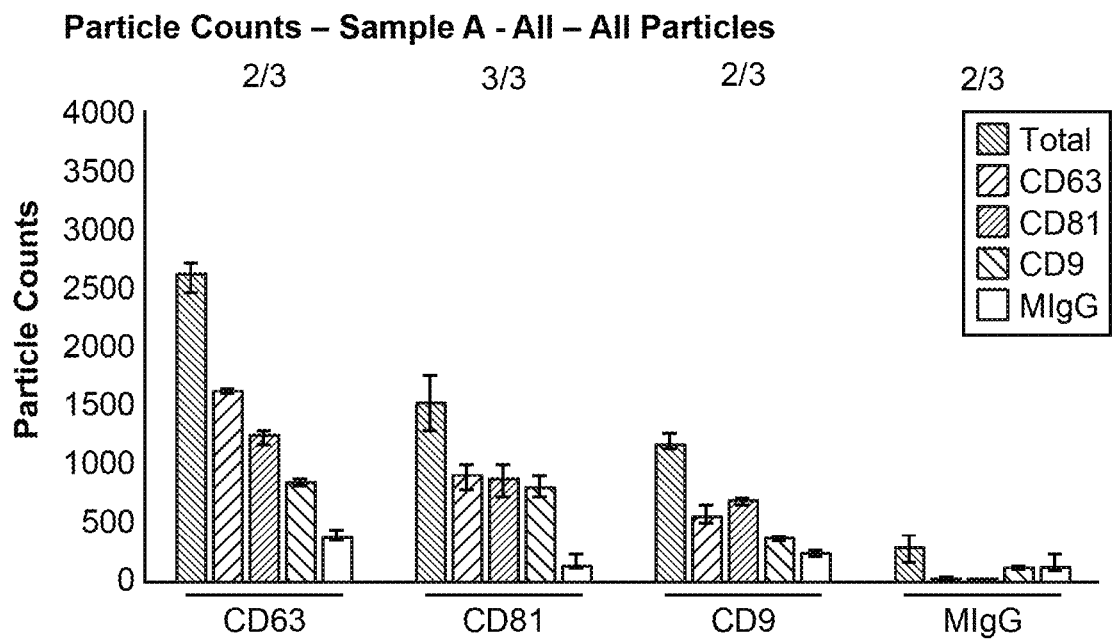
Figure 4D:
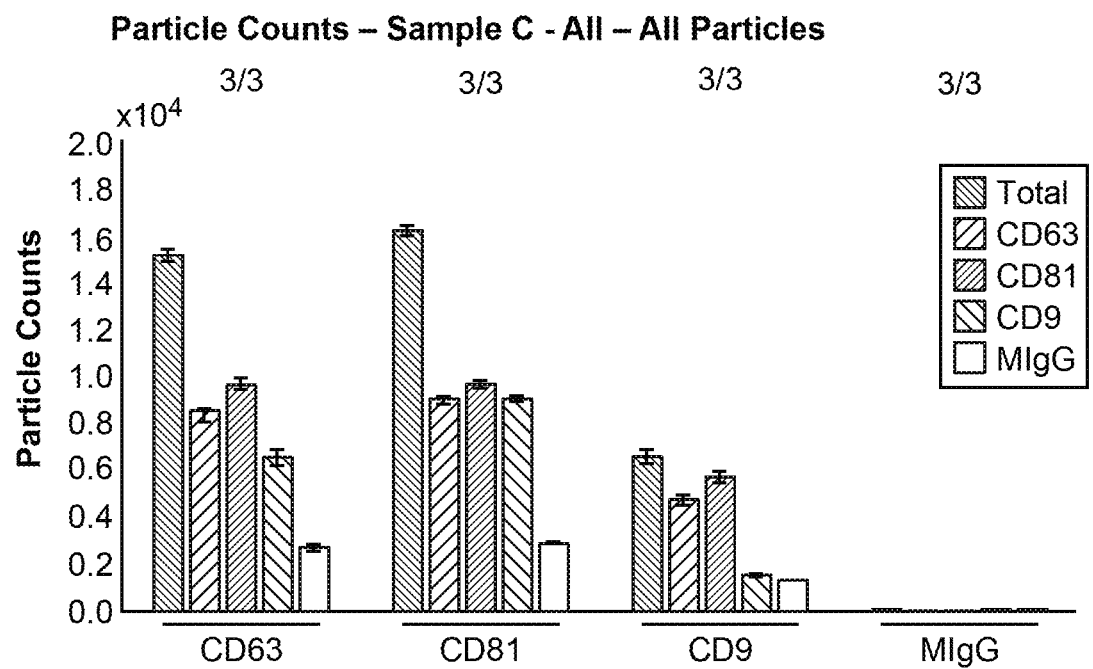
Figure 4E:
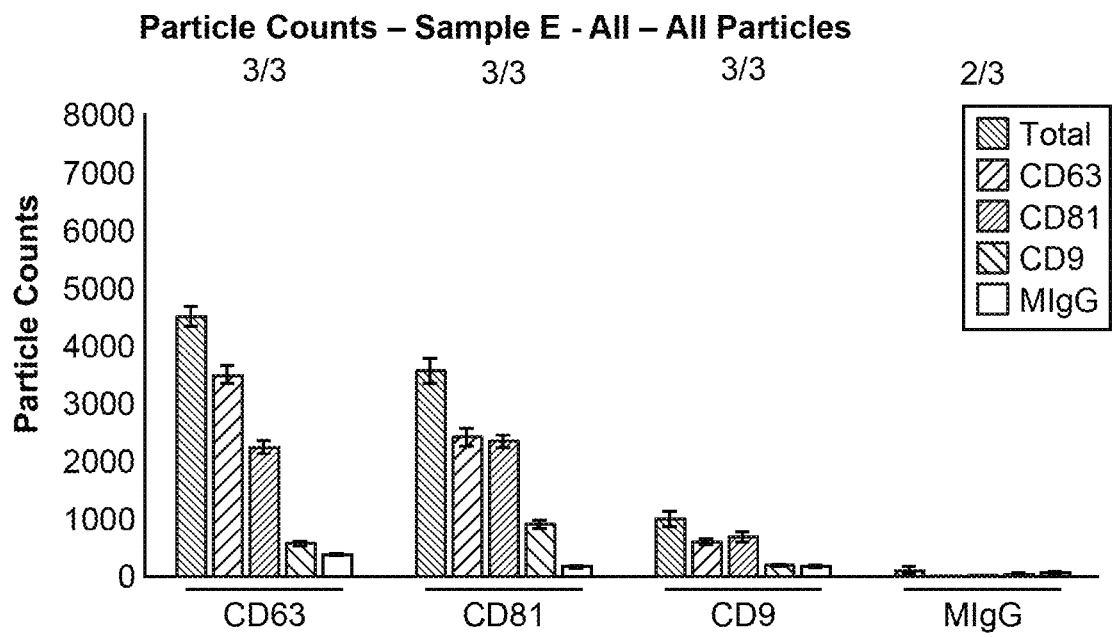
Figure 4F:
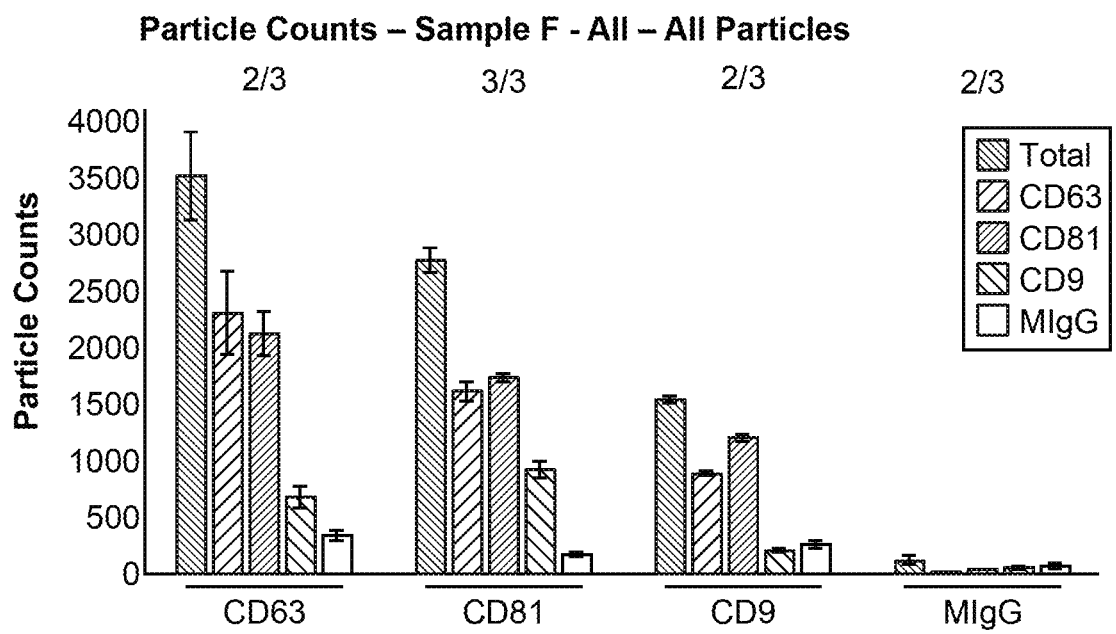
Figure 5A:
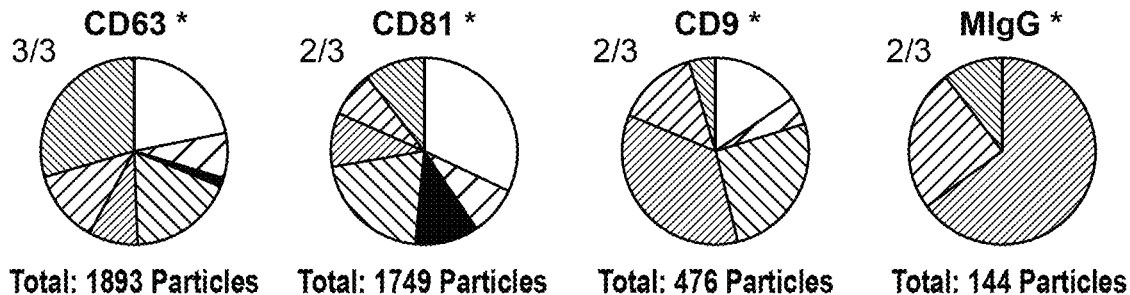
Figure 5B:
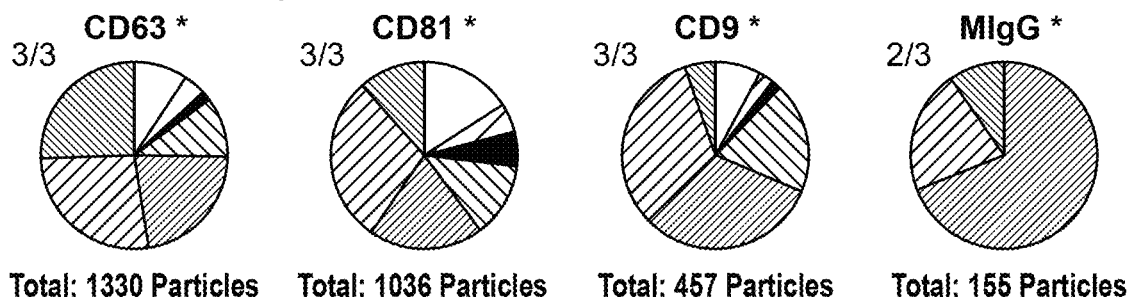
Figure 5C:
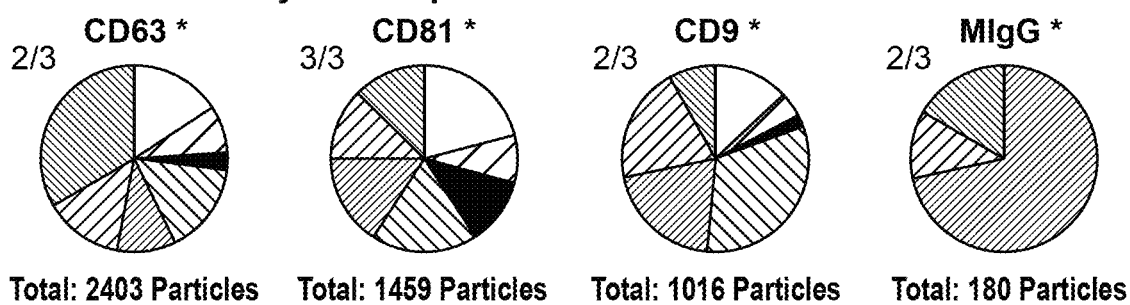
Figure 5D:
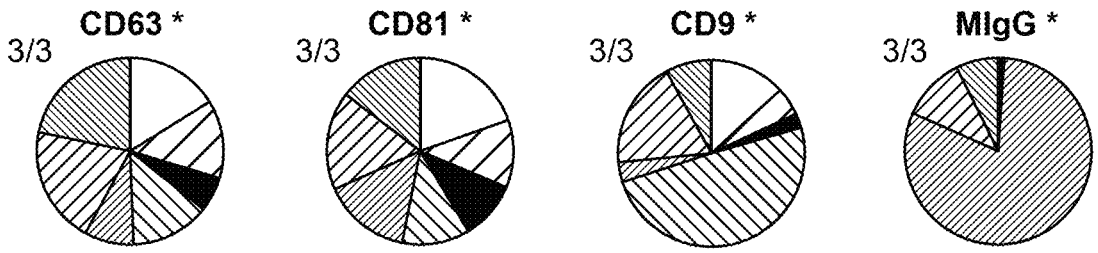
Figure 5E:
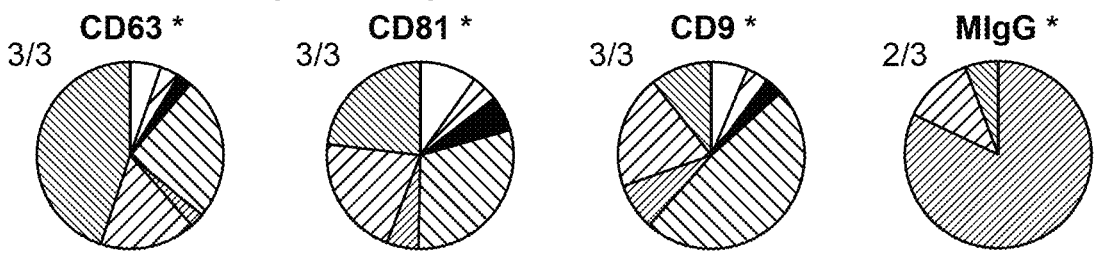
Figure 5F:
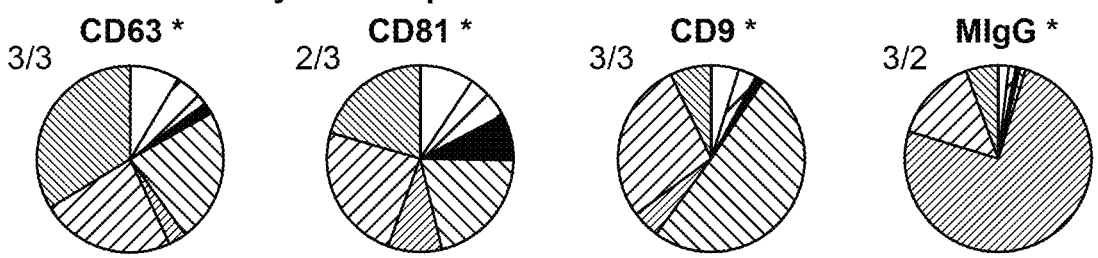

SP-IRIS. SP-IRIS results are shown in FIGS. 4A-4F. Briefly, the surface distribution of tetraspanin on Samples E and F (FIG. 4E & 4F) were closest to the nonlyophilized control samples 62822-02 (FIG. 4A) and Sample C (FIG. 4D). Further colocalization analysis of the SP-IRIS data, shown in FIGS. 5A-5F showed that Sample F (FIG. 5F) was the closest sample to the nonlyophilized controls (FIGS. 5A and 5D). In addition, exosomes lyophilized in Sample F (FIG. 6C) showed better integrity and tetraspanin expression on cell surface as compared to exosomes lyophilized in Sample B (FIG. 6A) and the control (Sample C, FIG. 6B) as shown by surface CD9 expression.

In aggregate, these results showed that the formulation of Sample F protect the EVs during lyophilization, and the compositions lyophilized in the formulation of Sample F are substantially the same as their non-lyophilized counterparts. The EVs lyophilized in Sample F showed almost as high Zeta potential as the control samples, meaning that Sample F protects EVs from aggregation during lyophilization. The EVs lyophilized in Sample F also maintained their integrity (i.e., did not release their cargo), surface marker expression, and shape. The instant results surprisingly showed that in Sample F, pre and post lyophilization exosomes were essentially equal with no sign of degradation of the cargo or loss of integrity of the exosome.

What is claimed is:

1. A composition comprising:
    0.3%-8% gamma cyclodextrin,
    2%40% sucrose,
    0.2%-10% trimethylglycine, and
    a biologic drug comprising an exosome, a liposome or a niosome, wherein the composition is a lyophilized composition.

2. The composition of claim 1, wherein the biologic drug comprises an exosome.

3. The composition of claim 1, wherein the composition comprises about 6% sucrose, about 1% gamma cyclodextrin and about 1% trimethylglycine and an exosome.

4. A method for stabilizing a biologic drug during lyophilization comprising mixing the biologic drug with a lyoprotectant blend before lyophilization, wherein the lyoprotectant blend comprises:
   0.3%-8% gamma cyclodextrin,
   2%-10% sucrose, and
   0.2%-10% trimethylglycine,
wherein the biologic drug comprises an exosome, a liposome or a niosome, wherein the mixture of the biologic drug and the lyoprotectant blend are lyophilized.

5. The method of claim 4, wherein the biologic drug comprises an exosome.

6. The method of claim 4, wherein the lyoprotectant blend comprises about 6% sucrose, about 1% gamma cyclodextrin and about 1% trimethylglycine and an exosome.

7. The method of claim 4, wherein the biologic drug comprises an exosome, wherein the exosome stabilized by the method during lyophilization retains at least 90% of its structural integrity when resolubilized.

8. A composition comprising an exosome, and further comprising:
   0.3%-8%: cyclic oligosaccharide-based polymer,
   2%-10%: sucrose, mannitol or trehalose,
   0.2%-10%: trimethylglycine, glycine, arginine, or a salt thereof, and
   wherein the composition is a lyophilized composition.

9. The composition of claim 8, wherein the cyclic oligosaccharide-based polymer comprises alpha cyclodextrin, beta cyclodextrin, gamma cyclodextrin, 2-hydroxypropyl-β-cyclodextrin, β-cyclodextrin sulfobutylether, a derivative thereof, or a combination thereof.

10. The composition of claim 8, wherein the cyclic oligosaccharide-based polymer comprises gamma cyclodextrin.

11. The composition of claim 8, wherein the composition comprises gamma cyclodextrin, sucrose, and trimethylglycine.

12. The composition of claim 8, wherein the composition comprises about 6% sucrose, about 1% gamma cyclodextrin and about 1% trimethylglycine.

13. A method for stabilizing an exosome during lyophilization comprising mixing the exosome with a lyoprotectant blend before lyophilization, wherein the lyoprotectant blend comprises:
   0.3%-8%: cyclic oligosaccharide-based polymer,
   2%-10%: sucrose, mannitol or trehalose,
   0.2%-10%: trimethylglycine, glycine, arginine, or a salt thereof, and
   wherein the mixture of the exosome and the lyoprotectant blend are lyophilized.

14. The method of claim 13, wherein the cyclic oligosaccharide-based polymer comprises alpha cyclodextrin, beta cyclodextrin, gamma cyclodextrin, 2-hydroxypropyl-β-cyclodextrin, β-cyclodextrin sulfobutylether, a derivative thereof, or a combination thereof.

15. The method of claim 13, wherein the cyclic oligosaccharide-based polymer comprises gamma cyclodextrin.

16. The method of claim 13, wherein the composition comprises gamma cyclodextrin, sucrose, and trimethylglycine.

17. The method of claim 13, wherein the composition comprises about 6% sucrose, about 1% gamma cyclodextrin and about 1% trimethylglycine.

* * * * *